US007820161B1

(12) United States Patent
Curd et al.

(10) Patent No.: US 7,820,161 B1
(45) Date of Patent: Oct. 26, 2010

(54) TREATMENT OF AUTOIMMUNE DISEASES

(75) Inventors: John G. Curd, Hillsborough, CA (US); Lori A. Kunkel, Oakland, CA (US); Antonio J. Grillo-Lopez, Rancho Santa Fe, CA (US)

(73) Assignees: Biogen Idec, Inc., Weston, MA (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/564,288

(22) Filed: May 4, 2000

Related U.S. Application Data

(60) Provisional application No. 60/133,018, filed on May 7, 1999, provisional application No. 60/139,621, filed on Jun. 17, 1999.

(51) Int. Cl.
*A61K 39/395* (2006.01)
(52) U.S. Cl. .............. 424/133.1; 424/144.1; 424/153.1; 424/173.1; 424/801; 424/810
(58) Field of Classification Search .............. 424/144.1, 424/153.1, 143.1, 173.1, 810; 514/2, 885; 530/388.22, 388.73, 389.6
See application file for complete search history.

(56) References Cited

U.S. PATENT DOCUMENTS

| | | | |
|---|---|---|---|
| 4,724,213 A | 2/1988 | Epstein | |
| 4,816,567 A | 3/1989 | Cabilly | |
| 4,861,579 A | 8/1989 | Meyer, Jr. et al. | |
| 4,975,278 A | 12/1990 | Senter et al. | |
| 5,417,972 A | 5/1995 | Bhat et al. | |
| 5,484,892 A | 1/1996 | Tedder et al. | |
| 5,500,362 A | 3/1996 | Robinson et al. | |
| 5,540,926 A | 7/1996 | Aruffo et al. | |
| 5,545,807 A | 8/1996 | Surani | |
| 5,587,459 A | 12/1996 | Uckun | |
| 5,589,369 A | 12/1996 | Seidman | |
| 5,591,669 A | 1/1997 | Krimpenfort | |
| 5,593,676 A | 1/1997 | Bhat et al. | |
| 5,595,721 A | 1/1997 | Kaminski et al. | |
| 5,648,267 A | 7/1997 | Reff et al. | |
| 5,677,165 A * | 10/1997 | de Boer et al. | |
| 5,677,180 A | 10/1997 | Robinson et al. | |
| 5,686,072 A | 11/1997 | Uhr et al. | |
| 5,693,780 A | 12/1997 | Newman et al. | |
| 5,721,108 A | 2/1998 | Robinson et al. | |
| 5,733,779 A | 3/1998 | Reff et al. | |
| 5,736,137 A * | 4/1998 | Anderson et al. | ........ 424/133.1 |
| 5,741,488 A | 4/1998 | Feldman et al. | |
| 5,776,456 A | 7/1998 | Anderson et al. | |
| 5,786,456 A | 7/1998 | Ledbetter et al. | |
| 5,795,569 A | 8/1998 | Bartley et al. | |
| 5,795,967 A | 8/1998 | Aggarwal et al. | |
| 5,843,398 A | 12/1998 | Kaminski et al. | |
| 5,843,439 A | 12/1998 | Anderson et al. | |
| 5,849,898 A | 12/1998 | Seed et al. | |
| 5,872,223 A | 2/1999 | Uckun | |
| 5,877,299 A | 3/1999 | Thomas et al. | |
| 6,001,358 A | 12/1999 | Black | |
| 6,015,542 A | 1/2000 | Kaminsky et al. | |
| 6,017,733 A | 1/2000 | Reff et al. | |
| 6,051,228 A | 4/2000 | Aruffo et al. | |
| 6,090,365 A | 7/2000 | Kaminsky et al. | |
| 6,113,898 A | 9/2000 | Anderson | |
| 6,120,767 A | 9/2000 | Robinson et al. | |
| 6,159,730 A | 12/2000 | Reff et al. | |
| 6,171,586 B1 | 1/2001 | Lam et al. | |
| 6,183,744 B1 | 2/2001 | Goldenberg | |
| 6,194,551 B1 | 2/2001 | Idusogie et al. | |
| 6,224,866 B1 | 5/2001 | Barbera-Guillem | |
| 6,242,195 B1 | 6/2001 | Idusogie et al. | |
| 6,270,766 B1 | 8/2001 | Feldman et al. | |
| 6,280,957 B1 | 8/2001 | Sayegh | |
| 6,287,537 B1 | 9/2001 | Kaminski et al. | |
| 6,306,393 B1 | 10/2001 | Goldenberg | |
| 6,315,998 B1 | 11/2001 | de Boer et al. | |
| 6,368,596 B1 | 4/2002 | Ghetie et al. | |
| 6,399,061 B1 | 6/2002 | Anderson et al. | |
| 6,410,319 B1 * | 6/2002 | Raubitschek et al. | |
| 6,410,391 B1 | 6/2002 | Zelsacher | |
| 6,451,284 B1 | 9/2002 | Raestetter et al. | |
| 6,455,043 B1 | 9/2002 | Grillo-López | |
| 6,514,513 B1 | 2/2003 | Sykes | |
| 6,528,624 B1 | 3/2003 | Idusogie et al. | |
| 6,538,124 B1 | 3/2003 | Idusogie et al. | |

(Continued)

FOREIGN PATENT DOCUMENTS

EP  332865  * 9/1989

(Continued)

OTHER PUBLICATIONS

Perotta et al., Blodd, vol. 10, Suppl. I Part 1-2, p. 88B, 1998.*

(Continued)

*Primary Examiner*—Ron Schwadron
(74) *Attorney, Agent, or Firm*—Sidley Austin LLP

(57) ABSTRACT

Methods are disclosed of treating rheumatoid arthritis in a human comprising administering to the human more than one intravenous dose of a therapeutically effective amount of rituximab and administering methotrexate to the human.

12 Claims, No Drawings

U.S. PATENT DOCUMENTS

| | | |
|---|---|---|
| 6,652,852 B1 | 11/2003 | Robinson et al. |
| 6,682,734 B1 | 1/2004 | Anderson et al. |
| 6,698,181 B2 | 3/2004 | Gehlsen |
| 6,737,056 B1 | 5/2004 | Presta et al. |
| 6,770,279 B1 | 8/2004 | Feldmann et al. |
| 6,846,476 B2 | 1/2005 | White |
| 6,893,625 B1 | 5/2005 | Robinson et al. |
| 6,896,885 B2 | 5/2005 | Hanna |
| 6,897,044 B1 | 5/2005 | Braslawsky et al. |
| 6,991,790 B1 | 1/2006 | Lam et al. |
| 7,074,403 B1 | 7/2006 | Goldenberg et al. |
| 7,122,637 B2 | 10/2006 | Presta |
| 2001/0018041 A1 | 8/2001 | Hanna et al. |
| 2001/0056066 A1 | 12/2001 | Bugelski et al. |
| 2002/0004587 A1 | 1/2002 | Miller et al. |
| 2002/0006404 A1 | 1/2002 | Hanna et al. |
| 2002/0009444 A1 | 1/2002 | Grillo-Lopez |
| 2002/0012665 A1 | 1/2002 | Hanna |
| 2002/0028178 A1 | 3/2002 | Hanna et al. |
| 2002/0039557 A1 | 4/2002 | White |
| 2002/0041847 A1 | 4/2002 | Goldenberg |
| 2002/0055122 A1 | 5/2002 | Sykes |
| 2002/0058029 A1 | 5/2002 | Hanna et al. |
| 2002/0071807 A1 | 6/2002 | Goldenberg |
| 2002/0128448 A1 | 9/2002 | Reff |
| 2002/0128488 A1 | 9/2002 | Yamakawa et al. |
| 2002/0155604 A1 | 10/2002 | Ledbetter |
| 2002/0159996 A1 | 10/2002 | Hariharan et al. |
| 2002/0197255 A1 | 12/2002 | Anderson et al. |
| 2002/0197256 A1 | 12/2002 | Grewal |
| 2003/0003097 A1 | 1/2003 | Reff et al. |
| 2003/0003098 A1 | 1/2003 | Strom |
| 2003/0021781 A1 | 1/2003 | Anderson et al. |
| 2003/0026801 A1 | 2/2003 | Weiner et al. |
| 2003/0036113 A1 | 2/2003 | Reff et al. |
| 2003/0082172 A1 | 5/2003 | Anderson |
| 2003/0095963 A1 | 5/2003 | Anderson |
| 2003/0103971 A1 | 6/2003 | Hariharan et al. |
| 2003/0124058 A1 | 7/2003 | Goldenberg |
| 2003/0133930 A1 | 7/2003 | Goldenberg et al. |
| 2003/0147885 A1 | 8/2003 | Anderson |
| 2003/0157108 A1 | 8/2003 | Presta |
| 2003/0157641 A1 | 8/2003 | Reff et al. |
| 2003/0158389 A1 | 8/2003 | Idusogie et al. |
| 2003/0166868 A1 | 9/2003 | Presta et al. |
| 2003/0180290 A1 | 9/2003 | Hariharan et al. |
| 2003/0180292 A1 | 9/2003 | Hanna et al. |
| 2003/0211038 A1 | 11/2003 | Raestetter et al. |
| 2003/0211107 A1 | 11/2003 | Hariharan et al. |
| 2003/0219433 A1 | 11/2003 | Hansen |
| 2004/0191256 A1 | 9/2004 | Raju |
| 2004/0202658 A1 | 10/2004 | Benyunes |
| 2004/0219203 A1 | 11/2004 | Griffiths |
| 2004/0228856 A1 | 11/2004 | Presta |
| 2004/0253250 A1 | 12/2004 | Ledbetter |
| 2005/0025764 A1 | 2/2005 | Watkins et al. |
| 2005/0032130 A1 | 2/2005 | Beresini et al. |
| 2005/0053602 A1 | 3/2005 | Brunetta |
| 2005/0095243 A1 | 5/2005 | Chan |
| 2005/0112060 A1 | 5/2005 | White |
| 2005/0112130 A1 | 5/2005 | Bhat |
| 2005/0118174 A1 | 6/2005 | Presta |
| 2005/0123540 A1 | 6/2005 | Hanna et al. |
| 2005/0158316 A1 | 7/2005 | Lam et al. |
| 2005/0158828 A1 | 7/2005 | Braslawsky et al. |
| 2005/0163708 A1 | 7/2005 | Robinson et al. |
| 2005/0163775 A1 | 7/2005 | Chan |
| 2005/0180975 A1 | 8/2005 | Hanna |
| 2005/0186205 A1 | 8/2005 | Anderson et al. |
| 2005/0186206 A1 | 8/2005 | Brunetta |
| 2005/0191297 A1 | 9/2005 | Brunetta |
| 2005/0191300 A1 | 9/2005 | Goldenberg et al. |
| 2005/0233382 A1 | 10/2005 | Presta |
| 2005/0255527 A1 | 11/2005 | Yang |
| 2005/0261478 A1 | 11/2005 | Ledbetter |
| 2005/0271658 A1 | 12/2005 | Brunetta et al. |
| 2005/0276803 A1 | 12/2005 | Chan et al. |
| 2006/0002930 A1 | 1/2006 | Brunetta et al. |
| 2006/0024295 A1 | 2/2006 | Brunetta |
| 2006/0024300 A1 | 2/2006 | Adams |
| 2006/0025576 A1 | 2/2006 | Miller et al. |
| 2006/0034835 A1 | 2/2006 | Adams |
| 2006/0051345 A1 | 3/2006 | Frohna |
| 2006/0051349 A1 | 3/2006 | Goldenberg |
| 2006/0057136 A1 | 3/2006 | Goldenberg |
| 2006/0062787 A1 | 3/2006 | Hitraya |
| 2006/0067930 A1 | 3/2006 | Adams et al. |
| 2006/0099662 A1 | 5/2006 | Chuntharapai et al. |
| 2006/0110387 A1 | 5/2006 | Brunetta |
| 2006/0121028 A1 | 6/2006 | Reff |
| 2006/0134111 A1 | 6/2006 | Agarwal |
| 2006/0135430 A1 | 6/2006 | Chan et al. |
| 2006/0171950 A1 | 8/2006 | Hariharan et al. |
| 2006/0172385 A1 | 8/2006 | Ernst et al. |
| 2006/0179501 A1 | 8/2006 | Chan et al. |
| 2006/0188495 A1 | 8/2006 | Barron et al. |
| 2006/0194290 A1 | 8/2006 | Presta |
| 2006/0194291 A1 | 8/2006 | Presta |
| 2006/0194954 A1 | 8/2006 | Idusogie et al. |
| 2006/0194957 A1 | 8/2006 | Presta |
| 2006/0218655 A1 | 9/2006 | Chan et al. |
| 2006/0233797 A1 | 10/2006 | Gujrathi |
| 2006/0240007 A1 | 10/2006 | Sanders |
| 2006/0240008 A1 | 10/2006 | Benyunes |
| 2006/0246004 A1 | 11/2006 | Adams et al. |
| 2006/0263349 A1 | 11/2006 | McCutcheon et al. |
| 2006/0263355 A1 | 11/2006 | Quan et al. |
| 2006/0275284 A1 | 12/2006 | Hanna et al. |
| 2006/0286100 A1 | 12/2006 | Hariharan et al. |
| 2006/0286101 A1 | 12/2006 | Hariharan et al. |
| 2007/0003544 A1 | 1/2007 | Hanna et al. |
| 2007/0009519 A1 | 1/2007 | Hariharan et al. |
| 2007/0020265 A1 | 1/2007 | Goldenberg |

FOREIGN PATENT DOCUMENTS

| | | |
|---|---|---|
| EP | 405972 A1 | 1/1991 |
| EP | 701130 A2 | 3/1996 |
| EP | 0 330 191 B1 | 10/1996 |
| EP | 0 340 109 B1 | 5/1997 |
| EP | 540859 B1 | 1/1998 |
| EP | 585943 B1 | 2/1998 |
| WO | 91/01133 | 2/1991 |
| WO | WO 91/13974 | 9/1991 |
| WO | WO 93/02108 | 2/1993 |
| WO | WO 93/021083 | 2/1993 |
| WO | WO 93/25673 | 12/1993 |
| WO | WO 94/27638 | 12/1994 |
| WO | WO 95/03770 | 2/1995 |
| WO | WO 95/09652 | * 4/1995 |
| WO | WO 95/14230 | 5/1995 |
| WO | 95/34320 | 12/1995 |
| WO | WO 96/34096 | 10/1996 |
| WO | WO 97/13529 | 4/1997 |
| WO | WO 97/31025 | 8/1997 |
| WO | WO 97/34633 | 9/1997 |
| WO | WO 97/45142 | 12/1997 |
| WO | 98/05357 | 2/1998 |
| WO | WO 98/04281 | 2/1998 |
| WO | WO 98/16254 | 4/1998 |
| WO | WO 98/42824 | 10/1998 |
| WO | WO 98/56418 A1 | 12/1998 |
| WO | WO 98/58964 A1 | 12/1998 |
| WO | WO 99/22764 A1 | 5/1999 |

| | | |
|---|---|---|
| WO | WO 99/30738 | 6/1999 |
| WO | 99/42077 | 8/1999 |
| WO | WO 99/51642 A1 | 10/1999 |
| WO | WO 99/54440 | 10/1999 |
| WO | WO 00/06694 | 2/2000 |
| WO | WO 00/09160 | 2/2000 |
| WO | WO 00/20864 A1 | 4/2000 |
| WO | WO 00/023573 | 4/2000 |
| WO | WO 00/27428 | 5/2000 |
| WO | WO 00/27433 | 5/2000 |
| WO | WO 0042072 A3 | 7/2000 |
| WO | WO 00/44788 A1 | 8/2000 |
| WO | 00/67795 | 11/2000 |
| WO | WO 00/67795 A1 | 11/2000 |
| WO | WO 00/67796 | 11/2000 |
| WO | WO 00/72333 A1 | 11/2000 |
| WO | WO 00/74718 | 12/2000 |
| WO | WO 00/76542 | 12/2000 |
| WO | WO 01/03734 | 1/2001 |
| WO | WO 01/10460 A1 | 2/2001 |
| WO | WO 01/10461 A1 | 2/2001 |
| WO | WO 01/10462 A1 | 2/2001 |
| WO | WO 01/13945 | 3/2001 |
| WO | WO 01/24823 | 4/2001 |
| WO | 01/34194 | 5/2001 |
| WO | WO 01/74388 A1 | 10/2001 |
| WO | WO 01/77342 A1 | 10/2001 |
| WO | WO 01/80884 A1 | 11/2001 |
| WO | WO 01/97858 | 12/2001 |
| WO | WO 02/04021 A1 | 1/2002 |
| WO | WO 02/34790 A1 | 5/2002 |
| WO | WO 02/060955 A2 | 8/2002 |
| WO | WO 02/079255 A1 | 10/2002 |
| WO | WO 02/096948 A2 | 12/2002 |
| WO | WO 02/102312 A2 | 12/2002 |
| WO | WO 2004/056312 | 7/2004 |
| WO | WO 2004/091657 | 10/2004 |
| WO | 2007/059188 | 5/2007 |

OTHER PUBLICATIONS

O'Dell et al., NEJM, 334:1287-91, 1996.*
Legal status (INPADOC) of EP1176981, pp. 1-6, http://v3.espscenet.com, retrieved Jan. 31, 2007.*
Johnston, "Rituximab-Associated Immune Thrombocytopenic Purpura" *Blood* 94 (10) :4386, Nov. 15, 1999.
Mow et al., "Rituximab for the Treatment of Refractory Immune Thrombocytopenic Purpura—Case Report" *Blood* 94:3526, Nov. 15, 1999.
Leget et al., "Use of rituximab, the new FDA-approved antibody" *Current Opinion in Oncology* 10(6):548-551 (Nov. 1998).
Protheroe et al., "Remission of inflammatory arthropathy in association with anti-CD20 therapy for non-Hodgkin's lymphoma" *Rheumatology (Oxford)* 38(11):1150-1152 (Nov. 1999).
Qu et al., "Carbohydrates engineered at antibody constant domains can be used for site-specific conjugation of drugs and chelates" *Journal of Immunological Methods* 213(2):131-144 (Apr. 15, 1998).
Rowan at al., "Cross-linking of the CAMPATH-1 antigen (CD52) mediates growth inhibition in human B- and T-lymphoma cell lines, and subsequent emergence of CD52-deficient cells" *Immunology* 95(3):427-436 (Nov. 1998).
Stein et al., "Epitope specificity of the anti-(B cell lymphoma) monoclonal antibody, LL2" *Cancer Immunology, Immunotherapy* 37(5):293-298 (Oct. 1993).
Theocharis et al., "Characterization of in vivo mutated T cell clones from patients with systemic lupus erythematosus" *Clinical Immunology & Immunopathology* 74(2):135-142 clones (Feb. 1995).
Introna et al., "Genetic modification of human T cells wtih CD20: a strategy to purify and lyse transduced cells with anti-CD20 antibodies" *Human Gene Therapy* 11(4):611-620 (Mar. 1, 2000).

McLaughlin et al., "Rituximab chimeric anti-CD20 monoclonal antibody therapy for relapsed indolent lyphoma: half of patients respond to a four-dose treatment program" *Journal of Clincal Oncology* 16(8):2825-2833 (Aug. 1998).
Verzeletti et al., "Herpes simplex virus thymidine kinase gene transfer for controlled graft-verses-host disease and graft-versus-leukemia: clinical follow-up and improved new vectors" *Human Gene Therapy* 9(15):2243-2251 (Oct. 10, 1998).
"Amgen Discontinues Development of MGDF" (press release) (Sep. 11, 1998).
Bellon et al., "Aerosol Administration of a Recombinant Adenovirus Expressing CFTR to Cystic Fibrosis Patients: A Phase I Clinical Trial" *Human Gene Therapy* 8:15-25 (1997).
Christ et al., "Gene therapy with recombinant adenovirus vectors: evaluation of the host immune response" *Immunology Letters* 57:19-25 (1997).
Cook et al., "Effective Treatment of Lymphoprofliferative Disease following Lung Transplantation using Monoclonal Anti-CD20 B-Cell Antibody" *The Journal of Heart and Lung Transplpantation* (abstract only) 18:84-85 (Jan. 1999).
Eisenberg, R., "Anti B-Cell Therapy in the Treatment of Autoimmune Disease" (Genentech Oncology and IDEC Pharmaceuticals Investigator-sponsored Protocol Concept Worksheet), May 29, 1998.
Gryn, J. (Clinical Research Proposal), May 6, 1998.
John et al., "Anti-CD20 monoclonal antibody for the treatment of post-transplant lympoproliferative disease in a pediatric heart transplant recipient." *Journal of Investigative Medicine* 4 (2):125A (Feb. 1999).
Knoell, "Clinical Aspects of Gene Therapy" *The Annals of Pharmacotherapy* 32:977-979 (Sep. 1998).
Latov, N., "Rituxan for Treatment of Neuropathy and IgM Monoclonal Gammopathy with Anti-MAG or Sulfatide Antibody Activity" (New Clinical Study Application), Nov. 16, 1998.
Levine et al., "IgM antibody-related polyneuropathies: B-cell depletion chemotherapy using Rituximab" *Neurology* 52:1701-1704 (May 12, 1999).
Looney, R.J. (Clinical Research Proposal) Jan. 15, 1999.
Nadler, L., "B Cell/Leukemia Panel Workshop: Summary and Comments (Chap. 1)" *Lymphocyte Typing II*, Renling et al., Springer Verlag vol. 2:3-37 and Appendix (1986).
Pestronk, A., "A study Rituxan in the treatment of polyneuropathies associated with serum IgM autoantibodies" (Clinical Research Proposal), 1998.
Saleh et al., "A Phase II Study of Rituxan in the Treatment of Immune Thrombocytopenic Purpura" (Clinical Research Proposal), 1998.
Anderson et al., "Expression of human B cell-associated antigens on leukemias and lymphomas: A model of human B cell differentiation" *Blood* 63(6):1424-1433 (1984).
Ballester et al., "Rituximab can be safely included as part of high-dose therapy/autologous stem cell transplantation for patients with Non-Hodgkin's lymphoma" *Blood* (Abstract #4552) 92(10 Suppl. 1 part 1-2):360b-361b (Nov. 15, 1998).
Buckstein et al., "The effects of in vivo purging with Rituxan on stem cell mobilization efficacy, harvest purity, cytokine profile and engraftment in patients with relapsed follicular lymphoma undergoing autologous stem cell transplant" *Blood* (Abstract #2672) 92(10 Suppl. 1 Part 1-2):647a (1998).
Bussel, J.B., "Autoimmune Thrombocytopenic Purpura" *Hematology—Oncology Clinics of North America* 4(1):179-191 (Feb. 1990).
Demidem et al., "Chimeric anti-CD20 (IDEC-C2B8) monoclonal antibody sensitizes a B cell lymphoma cell line to cell killing by cytotoxic drugs" *Cancer Biotherapy & Radiopharmaceuticals* 12(3):177-186 (1997).
Einfeld et al., "Molecular cloning of the human B cell CD20 receptor predicts a hydrophobic protein with multiple transmembrane domains" *EMBO Journal* 7(3):711-717 (1988).
Faye et al., "Anti-CD20 monoclonal antibody for post-transplant lymphoproliferative disorders" *Lancet* 352:1285 (Oct. 17, 1998).
Flinn et al., "In vivo purging an adjuvant immunotherapy with Rituximab during PBSC transplant or NHM" *Blood* (Abstract #2673) 92(10 Suppl 2 part 1-2):648a (Nov. 15, 1998).

George et al., "Idiopathic Thrombocytopenic Purpura: A Practice Guideline Developed by Explicit Methods for The American Society of Hematology" *Blood* 88(1):3-40 (Jul. 1, 1996).

Kiesel et al., "Removal of cells from a malignant B-cell line from bone marrow with immunomagnetic beads and with complement and immunoglobulin switch variant mediated cytolysis" *Leukemia Research* 11(12):1119-1125 (1987).

Korholz et al., "Humoral immunodeficiency in patients after bone marrow transplantation" *Bone Marrow Transplantation* 18:1123-1130 (1996).

Lee et al., "Rituxan in the treatment of cold agglutinin disease" *Blood* 92(9):3490-3491 (Nov. 1, 1998).

Maloney et al., "The anti-tumor effect of monoclonal anti-CD20 antibody (mAb) therapy includes direct anti-proliferative activity and induction of apoptosis in CD20 positive non-Hodgkin's lymphoma (nhl) cell lines" *Blood* (Abstract #2535) 88(10):637a (1996).

Nadler et al., "B4, a human B lymphocyte-associated antigen expressed on normal, mitogen-activated, and malignant B lymphocytes" *J. Immunol*, 131(1):244-250 (Jul. 1983).

Nadler et al., "Diagnosis and treatment of human leukemias and lymphomas utilizing monoclonal antibodies" *Progress in Hematology*, Brown, E., Grune & Stratton, Inc. vol. XII:187-225 (1981).

Notoya et al., "Chronic cold agglutinin disease accompanied with an increase of $CD20^+/CD5^+$ cells; a case report" *The Japanese Journal of Clinical Hematology* (English language abstract of attached Japanese article) 35(9):881-885 (Sep. 1994).

Oooto et al., "Quantitative Flowcytometric Analysis of B Cell Surface Antigens in Patients with Autoimmune Diseases" *The Japanese Journal of Clinical Pathology* (English language abstract of attached Japanese article) 43(4):381-384 (Apr. 1995)

Paulus et al., "Analysis of improvement in individual rheumatoid arthritis patients treated with disease-modifying antirheumatic drugs, based on the findings in patients treated with placebo" *Arthritis Rheum*. 33(4):477-484 (Apr. 1990).

Piascik, P., "New therapeutic monoclonal antibodies target kidney transplant rejection and cancer" *Journal of the American Pharmaceutical Association* 38(3):379-380.

Reff et al., "Depletion of B cells in vivo by a chimeric mouse human monoclonal antibody to CD20" *Blood* 83(2):435-445 (Jan. 15, 1994).

Shan et al., "Apoptosis of malignant human B cells by ligation of CD20 with monoclonal antibodies" *Blood* 91(5):1644-1652 (Mar. 1, 1998).

Tedder et al., "The B cell surface molecule B1 is functionally linked with B cell activation and differentiation" *The Journal of Immunology* 135(2):973-979 (1985).

Tedder et al., 'The CD20 surface molecule of B lymphocytes functions Biochem. (Abstract # M 023) 14D:195 (1990).

Vaile et al., "Bowel Permeability and CD45R0 Expression on Circulating CD20+ B Cells in Patients with Ankylosing Spondylitis and Their Relatives" *The Journal of Rheumatology* 26(1):128-135 (1999).

Valentine et al., "Phosphorylation of the CD20 phosphoprotein in resting B lymphocytes" *Journal of Biological Chemistry* 264(19):11282-11287 (Jul. 5, 1989).

Vassilev et al., "Antibodies to the CD5 molecule in normal human immunoglobulins for therapeutic use (intravenous immunoglobulins, IVIg)" *Clin. Exp. Immunol*, 92:369-372 (Feb. 25, 1993).

Watson et al., "A case of geminal center formation by CD45R0 T and CD2O B lymphocyte in rheumatoid arthritic subchondral bone: proposal for a two-compartment model of immune-mediated disease with implications for immunotherapeutic strategies" *Clinical Immunology and Immunopathology* 73(1):27-37 (1994).

Wilkes et al., "Preferential production of IgG2 antibodies by parenchymal lung B-lymphocytes during lung allograft rejection" *Transplantation Proceedings* 29:1891-1895 (1997).

Yokose et al., "Low-grade B cell lymphoma of mucosa-associated lymphoid tissue in the thymus of a patient with rheumatoid arthritis" *Pathology International* 48:74-81 (1998).

Yu and Lennon, "Mechanism of Intravenous immune globulin therapy in antibody-mediated autoimmune diseases" *New England J. of Medicine* 340(3):227-228 (Jan. 21, 1999).

Friend et al., "Phase I study of an engineered aglycosylated humanized CD3 antibody in renal transplant rejection" *Transplantation* 68:1625-1626 (Dec. 15, 1999).

U.S. Appl. No. 60/105,014, filed Oct. 20, 1998, Raubitschek et al.

Edwards, J.C.W. et al. "Sustained improvement in rheumatoid arthritis following a protocol designed to deplete B lymphocytes." Rheumatology, vol. 40, 2001. pp. 205-211.

Edwards, J.C.W. et al. "B-lymphocyte depletion therapy in rheumatoid arthritis and other autoimmune disorders." Biochemical Society Transactions, vol. 30, part 4, 2002. pp. 824-828.

Leandro, M.J. et al. "Clinical outcome in 22 patients with rheumatoid arthritis treated with B lymphocyte depletion." Ann Rheum Dis, vol. 61, 2002. pp. 883-888.

Leandro, M.J. et al. "An Open Study of B Lymphocyte Depletion in Systemic Lupus Erythematosus." Arthritis & Rheumatism, vol. 46, No. 10, Oct. 2002. pp. 2673-2677.

Matthews, Robert. "Medical Heretics." New Scientist, Apr. 7, 2001. pp. 34-37.

Stasi, R. et al. "Rituximab chimeric anti-CD20 monoclonal antibody treatment for adults with chronic idiopathic thrombocytopenic purpura." Blood, vol. 98, No. 4, Aug. 2001. pp. 952-957.

Pai-Scherf et al. "A Phase II Clinical Trial of Suppression of Human Antimouse Antibody and Human Antitoxin Response to Immunotoxin LMB-1 by Rituximab" (Clinical Research Proposal), Sep. 25, 1998.

Pescovitz. "Pilot Study of Rituxan (anti-CD20) for the reduction of high titered anti-HLA antibodies in patients with renal failure awaiting renal transplant" (Clinical Trial Proposal), Mar. 21, 1999.

Pescovitz. "Pilot Study of Rituxan (anti-CD20) for the reduction of high titered anti-HLA antibodies in patients with renal failure awaiting renal transplant" (Letter to Dr. Grillo-Lopez and Protocol Concept Sheet), Oct. 13, 1998.

Sollinger. Letter to Dr. Bonni S. Dutcher, Dec. 23, 1998.

Sollinger. "Phase 2 trial using Rituxan to desensitize patients awaiting renal transplant" (Investigator Initiated Protocol Concept Worksheet), Jan. 5, 1999.

Arnada, J.M. et al. "Anti-CD20 Monoclonal Antibody (Rituximab) Therapy for Acute Cardiac Humoral Rejection: A Case Report", Transplantation, 2000, pp. 907-910.

Ratanatharathorn, V. et al. "Anti-CD20 Monoclonal Antibody Treatment of Refractory Immune-Mediated Thrombocytopenia in a Patient with Chronic Graft-versus-Host Disease", Annals of Internal Medicine, Aug. 2000, pp. 275-279.

Anasetti, C. et al. "Graft-v-Host Disease is Associated with Autoimmune-like Thrombocytopenia", The Journal of the American Society of Hematology, vol. 73, No. 4, Mar. 1989, pp. 1054-1058.

Aggarwal A, et al., Rituximab: an anti-CD20 antibody for the treatment of chronic refractory immune thrombocytopenic purpura, South Med J. Oct. 2002;95(10):1209-12.

Anderson D, et al., A Primatized MAb to Human CD4 Causes Receptor Modulation, without Marked Reduction in $CD4^+$ T Cells in Chimpanzees: In Vitro and In Vivo Characterization of a MAb (IDEC-CE9.1) to Human CD4, Clinical Immunology and Immunopathology, vol. 84, No. 1, Jul., pp. 73-84, 1997, Article No. II974363.

Anolik JH et al., Rituximab improves peripheral B cell abnormalities in human systemic lupus erythematosus, Arthritis Rheum. Nov. 2004;50(11):3580-90.

Arzoo K, et al., Treatment of refractory antibody mediated autoimmune disorders with an anti-CD20 monoclonal antibody (rituximab), Ann Rheum Dis 2002;61:922-924.

Berrih S., et al., Interferon-gamma modulates HLA class II antigen expression on cultured human thymic epithelial cells, J Immunol. Aug. 1985;135(2):1165-71.

Berentsen S, et al., Rituximab for primary chronic cold agglutinin disease: a prospective study of 37 courses of therapy in 27 patients, Blood. Apr. 15, 2004;103(8):2925-8.

Bonilla FA et al., Primary immunodeficiency diseases, J Allergy Clin Immunol. Feb. 2003;111(2 Suppl):S571-81.

Buckley CD, Treatment of rheumatoid arthritis, BMJ vol. 315, Jul. 26, 1997, pp. 236-238.

Buckley RH, Primary cellular immunodeficiencies, J Allergy Clin Immunol. May 2002;109(5):747-57.

Bujiah J, et al., Detection of class II antigens on human nasal cartilage, Am J Otolaryngol. Sep.-Oct. 1990; 11(5):339-44.
Choy EHS, et al., Cytokine Pathways and Joint Inflammation in Rheumatoid Arthritis, N Engl J Med, vol. 344, No. 12, Mar. 22, 2001, pp. 907-915.
Choy EHA, et al., Repeat-cycle study of high-dose intravenous 4162W94 anti-CD4 humanized monoclonal antibody in rheumatoid arthritis. A randomized placebo-controlled trial, Rheumatology 2002;41:1142-1148.
Coll AP, et al., Rituximab therapy for the type B syndrome of severe insulin resistance, N. Engl J Med. Jan. 15, 2004;350(3):310-1.
Cragg MS, et al., Antibody specificity controls in vivo effector mechanisms of antiCD20 reagents, Blood, Apr. 1, 2004, vol. 103, No. 7, pp. 2738-2743.
DeNardo GL, et al., Characterization of Human IgG Antimouse Antibody in Patients with B-Cell Malignancies, Clinical Cancer Research, vol. 9, 4013s-4021s, Sep. 1, 2003 (Suppl.).
Dupuy A, et al., Treatment of refractory pemphigus vulgaris with rituximab (anti-Cd20 monoclonal antibody), Arch Dermatol. Jan. 2004;140(1):91-6.
Edwards JCW, et al., Rheumatoid Arthritis: The Predictable Effect of Small Immune Complexes in Which Antibody Is Also Antigen, British Journal of Rheumatology 1998;37:126-130.
Edwards JCW, et al., Do self-perpetuating B lymphocytes drive human autoimmune disease?, Immunology 1999;97:188-196.
Edwards JCW, et al., Efficacy of B-Cell-Targeted Therapy with Rituximab in Patients with Rheumatoid Arthritis, The New England Journal of Medicine, Jun. 17, 2004; 350:2572-71.
Endo T, et al., Successful treatment with rituximab for autoimmune hemolytic anemia concomitant with proliferaton of Epstein-Barr virus and monoclonal gammopathy in a post-nonmyeloablative stem cell transplant patient, Ann Hematol. Feb. 2004;83(2):114-6.
Espana A, et al., Long-term complete remission of severe pemphigus vulgaris with monoclonal anti-CD20 antibody therapy and immunophenotype correlations, J Am Acad Dermatol. Jun. 2004;50(6);974-6.
Gajra A, et al., Response of myasthenia gravis to rituximab in a patient with non-Hodgkin lymphoma, Am H. Hematol. Oct. 2004;77(2):196-7.
Geha RS, Antibody deficiency syndromes and novel immunodeficiences, Pediatr Infect Dis J. May 1988;7(5 Suppl):S57-60.
Goebeler M, et al., Rapid response for treatment-resistant pemphigus foliaceus to the anti-CD20 antibody rituximab, Br J Dermaol. Oct. 2003;149(4):899-901.
Graus F, et al., Complex antigens in normal human dorsal root ganglia, J Neurol Sci. Sep. 1990;98(2)-3):203-11.
Hamer KC, et al., Normalization of anticardiolipin antibodies following rituximab therapy for marginal zone lymphoma in a patient with Sjorgen's syndrome, Rheumatology (Oxford)., Oct. 2004;43(10):1309-10.
Heath M, et al., Evidence-based evaluation of immunology therapy for the cutaneous manifestations of lupus, Adv Dermatol. 2004;20:257-91.
Hepburn TW, et al., Antibody-medicated stripping of CD4 from lymphocyte cell surface in patients with rheumatoid arthritis, Rheumatology 2003;42:544-61.
Jonasson L, et al., Expression of class II transplantation antigen on vascular smooth muscle cells in human atherosclerosis, J Clin Invest. Jul. 1985;76(1):125-31.
Kawai T et al., Thromboembolic complications after treatment with monoclonal antibody against CD40 ligand, Feb. 2000, vol. 6, No. 2, pp. 1-4.
Kazkaz H, et al., Anti B cell therapy (rituximab) in the treatment of autoimmune diseases, Curr Opin Pharmacol. Aug. 2004;4(4):398-402.
Kinn SR, et al., Detection and quantation of HLA class II molecules on keratinocytes by quantitative immunofluorescence, J Immunol. Methods. Dec. 5, 1990; 134(2):243-51.
Kon OM, et al., The effects of an anti-CD4 monoclonal antibody, keliximab, on peripheral blood CD4+T-cells in asthma. Eur Respir J 2001; 18:45-52.

Laguens G, et al., Demonstration and characterization of HLA-DR positive cells in the stroma of human endometrium, J Reprod Immunol. Sep. 1990;18(2):179-86.
Levy, O. et al., Results of a Placebo-Controlled, Multicenter Trial Using a Primatized® Non-Depleting, Anti-CD4 Monoclonal Antibody in the Treatment of Rheumatoid Arthritis, American College of Rheumatology, vol. 39, No. 9 (Supplement) Sep. 1996.
Lloyd RV, et al., Detection of HLA-DR antigens in paraffin-embedded thyroid epithelial cells with a monoclonal antibody, AM J Pathol. Jul. 1985;120(1):106-11.
Looney RJ, Treating human autoimmune disease by depleting B cells, Ann Rheum Dis 2002;61:863-866.
Looney RJ, et al., B cell depletion as a novel treatment for systemic lupus erythematosus: a phase I/II dose-escalation trial of rituximab, Arthritis Rheum. Aug. 2004;50(8):2580-9.
Looney RJ, et al., B cells as therapeutic targets for rheumatic diseases, Current Opinion in Rheumatology 2004, 16:180-185.
Maloney DC, et al., IDEC-C2B8 (Rituximab) Anti-CD20 Monoclonal Antibody Therapy in Patients with Relapsed Low-Grade Non-Hodgkin's Lymphoma, Blood, vol. 90, No. 6, Sep. 15, 1997: pp. 2188-2195.
Mavragani CP, et al., A case of reversible posterior leucoencephalopathy syndrome after rituximab infusion, Rheumatology (Oxford). Nov. 2004;43(11):1450-1.
Moreland L, et al., Double-blind, Placebo-Controlled Multicenter Trial Using Chimeric Monoclonal Anti-CD4 Antibody, cM-T412, in Rheumatoid Arthritis Patents Receiving Concomitant Methotrexate, Arthritis & Rheumatism, vol. 38, No. 11, Nov. 1995, pp. 1581-1588.
Ochs HD, et al., X-linked immunodeficiencies, Curr Allergy Asthma Rep. Sep. 2004;4(4):339-48.
Okamoto H, et al., Rituximab for rheumatoid arthritis, N Engl J Med. Oct. 28, 2004;2351(18):1909.
Olsen NJ, et al. A Double-Blind, Placebo-Controlled Study of Anti-CD5 Immunoconjugate in Patients with Rheumatoid Arthritis, Arthritis & Rheumatism, vol. 39, No. 7, Jul. 1996, pp. 1102-1108.
Oshima SE, Selective signal transduction through the CD3 or CD2 complex is required for class II MHC expression by human T cells, J. Immunol. Dec. 15, 1990;145(12):4018-25.
Ottonello PM et al., Monoclonal Lym-1 Antibody-Dependent Lysis of B-Lymphoblastoid Tumor Targets by Human Complement and Cytokine-Exposed Mononuclear and Neutrophilic Polymorphononuclear Leukocytes, Blood, vol. 87, No. 12, Jun. 15, 1996, pp. 5171-5178.
Panayi GS, T-cell-dependent pathways in rheumatoid arthritis, Current Opinion in Rheumatology 1997; 9:236-240.
Papadalcis KA, et al., Anti-CD20 chimeric monoclonal antibody (rituximab) treatment of immune mediated thrombocytopenia associated with Crohn's disease, Gastroenterology. Feb. 2003;124(2):583.
Polyak M, et al., Alanine-170 and proline-172 are critical determinants for extracellular CD20 epitopes; heterogeneity in the fine specificity of CD20 monoclonal antibodies is defined by additional requrements imposed by both amino acid sequence and quaternary structure, Blood, May 1, 2002, vol. 99, No. 9.
Pulczynski S et al., Antibody-Induced Modulation and Intracellular Transport of CD10 and CD19 Antigens in Human B-Cell Lines: an inununofluourescence and Immunoelectron Microscopy Study, Blood, Vol. 81, No. 6 (Mar. 15, 1993): pp. 1549-1557.
Qian Gong et al., Importance of Cellular Microenvironmental and Circulatory Dynamics in B Cell Immunotherapy, Journal of Immunology, 2005, 174: 817-826.
Quinn J, et al., Evan's syndrome complicating multicentric Castleman's disease—dramatic response to rituximab, Eur J Haematol. Nov. 2004;73(5):384-5.
Reid CD, et al., Identification of hematopoietic progenitors of macrophages and dendritic Langerhans cells (DL-CFU) in human bone marrow and peripheral blood, Blood. Sep. 15, 1990;76(6):1139-49.
Rojas-Garcia R, et al., Chronic neuropathy with IgM anti-ganglioside antibodies: lack of long term response to rituximab, Neurology. Dec. 23, 2003;61(12):1814-6.

Saigal K, et al., Hypocomplementemic urticarial vasculitis with angioedema, a rare presentation of systemic lupus erythematosus: rapid response to rituximab, J Am Acad Dermatol. Nov. 2003;49(5 Suppl):S283-5.

Shan D, et al., Constitutive Endocytosis and Degradation of CD22 by Human B Cells, The Journal of Immunology, 1995, 154: 4466-4475.

Shanafelt TD, et al., Rituximab for immune cytopenia in adults: idiophathic thrombocytopenic purpura, autoimmune hemolytic anemia, and Evans syndrome, Mayo Clin Proc. Nov. 2003;78(11):1340-6 .

Siddiqui K et al., Chronic ataxic neuropathy with cold agglutinins: atypical phenotype and response to anti-CD20 antibodies, Neurology. Nov. 11, 2003;61(9):1307-8.

Schiff C, et al., Autosomal primary Immunodeficiencies affecting human bone marrow B-cell differentiation, Immunol Rev. Dec. 2000; 178:91-8.

Schiff M, Emerging Treatments for Rheumatoid Arthritis, Jan. 27, 1997, vol. 102, pp. 1A-15S.

Shvidel L, et al., Intractable autoimmune hemolytic anemia B cell chronic lymphocytic leukemia resolved by Rituximab, Leuk Lymphoma. Jul. 2004;45(7):1493-4.

Tabibzadeh S, et al., Immunoreactivity of human endometrium: correlation with endometrial dating, Fertil Steril. Oct. 1990;554(4):624-31.

Tedder FT, et al., The B Cell Surface Molecule B1 Is Functionally Linked With B Cell Activation and Differentiation, The Journal of Immunology, vol. 135, No. 2, Aug. 1985, pp. 973-979.

Todd I, et al. Interferon-gamma induces HLA-DR expression by thyroid epithelium, Clin Exp Immunol. Aug. 1985;61(2):265-73.

Tsokos Gc, B cells, be gone -B-cell depletion in the treatment of rheumatoid arthritis, N Engl J Med. Jun. 17, 2004;17;350(25):2546-8.

Uchida J et al., The Innate Mononuclear Phagocyte Network Depletes B Lymphocytes through Fc Receptor-dependent Mechanisms during Anti-Cd20 Antibody Immunotherapy, Journal of Experimental Medicine, vol. 199, No. 12, Jun. 21, 2004, 1659-1669.

Vaigot P, et al., Detection of distinct subpopulations of Langerhans cells by flow cytometry and sorting, Cytometry, Sep. 1985; 6(5):422-7.

Virgolini L, et al., Anti-CD20 monoclonal antibody (rituximab) in the treatment in of autoimmune disease. Successful result in refractory Pemphigus vulgaris: report of a case, Haematologica. Jul. 2003;88(7).

Virgolini L, et al., Rituximab in autoimmune disease, Biomed Pharmacother. Jun. 2004;58(5):299-309.

Webster D, et al., Prompt Response to Rituximab of Severe Hemolytic Anemia With Both Cold and Warm Autoantibodies, American Journal of Hematology, 75:258-259 (2004).

Wendling D, ,et al., A Randomized, Double Blind, Placebo Controlled Multicenter Trial of Murine Anti-CD4 Monoclonal Antibody Therapy in Rheumatoid Arthritis, The Journal of Rheumatology 1998; 25;8; 1458-1461.

Wylam ME, et al., Succesful treatment of refractory myasthenia gravis using rituximab: a pediatric case report, J Pediatr. Nov. 2003;143(5):674-7.

Wicks I, et al., Autologous hemopoietic stem cell transplantation: A possible cure for rheumatoid arthritis?, Arthritis & Rheumatism, vol. 40, No. 6, Jun. 1997, pp. 1005-1011.

Yocum DE, T Cells: Pathogenic Cells and Therapeutic Targets in Rheumatoid Arthritis, Seminars in Arthritis and Rheumatism, vol. 29, No. 1, Aug. 1999: pp. 27-35.

Yong VW, Morphologic heterogeneity of human adult astrocytes in culture: correlation with HLA-DR expression, J Neurosci Res. Dec. 1990; 27(4):678-88.

Xiao BG, Link H, Antigen-specific T cells in autoimmune diseases with a focus on multiple sclerosis and experimental allergic encephalomyelitis, CMLS, Cell. Mol. Life Sci. 56 (1999) 5-21.

Chari et al., "Immunoconjugates containing novel maytansinoids: Promising anticancer drugs," *Cancer Res.* 52:127-131, 1992.

Clark et al., "Role of the Bp35 cell surface polypeptide in human B-cell activation," *Proc. Natl. Acad Sci. USA* 82:1766-1770, 1985.

Daëron, "Fc receptor biology," *Ann. Rev. Immunol.* 15:203-234, 1997.

Decker et al., "Azathioprine and cyclophosphamide as slow-acting drugs for rheumatoid arthritis," *Am. J. Med.* 75(6A):74-78, abstract, 1983.

Durie et al., "The role of CD40 and its ligand (gp39) in peripheral and central tolerance and its contribution to autoimmune disease," *Res. Immunol.* 145:200-205, 1994.

Engel et al., "Identification of the ligand-binding domains of CD22, a member of the immunoglobulin superfamily that uniquely binds a sialic acid-dependent ligand," *J. Exp. Med.* 181:1581-1586, 1995.

Goronzy et al., "B cells as a therapeutic target in autoimmune disease," *Arthritis Res. Ther.* 5:131-135, 2003.

Hinman et al., "Preparation and characterization of monoclonal antibody conjugates of the calicheamicins: a novel and potent family of antitumor antibiotics," *Cancer Res.* 53:3336-3342, 1993.

Janeway, "Autoimmune disease: immunotherapy by peptides?" *Nature* 341:482-483, 1989.

Janeway, Immunobiology, The Immune System in Health and Disease, 579-587, 4$^{th}$ Ed., Elsevier Science Ltd., Garland Publishing, NY, 1999.

Morrison et al., "Chimeric human antibody molecules: mouse antigen-binding domains with human constant region domains," *Proc. Natl. Acad. Sci. USA* 81:6851-6855, 1984.

Neuberger et al., "Recombinant antibodies possessing novel effector functions," *Nature* 312:604-608, 1984.

Nitschke et al., "CD22 is a negative regulator of B-cell receptor signaling," *Curr. Biol.* 7:133-143, 1997.

Noelle et al., "Cognate interactions between helper T cells and B cells," *Immunol. Today* 11: 361-368, 1990.

Press et al., "Monoclonal antibody 1F5 (anti-CD20) serotherapy of human B cell lymphomas," *Blood* 69:584-591, 1987.

Ratanatharathom et al., "Anti-CD20 chimeric monoclonal antibody treatment of refractory immune-mediated thrombocytopenia in a patient with chronic graft-versus-host disease," *Annals of Int. Med.* 133(4): 275-279, 2000.

Ravetch et al., "Fc receptors," *Ann. Rev. Immunol.* 9:457-492, 1991.

St. Clair, "Interleukin 10 treatment for rheumatoid arthritis," *Ann. Rhem. Dis.* 58(Suppl. 1):I99-I102, 1999.

Vitetta et al., "Cellular interactions in the humoral immune response," *Adv. Immunol.* 45:1-105,1989.

Epstein et al., "Two New Monoclonal Antibodies, Lym-1 and Lym-2, Reactive with Human B-Lymphocytes and Derived Tumors, with Immunodiagnostic and Immunotherapeutic Potential", Cancer Research 47, 830-840, Feb. 1, 1987.

Maloney et al., Phase I Clinical Trial Using Escalating Single-Dose Infusion of Chimeric Anti-CD20 Monoclonal Antibody (IDEC-C2B8) in Patients With Recurrent B-Cell Lymphoma, Blood, vol. 84, No. 8, Oct. 15, 1994, pp. 2457-2466.

J Elliott et al., "Semi-Specific Immuno-Absorption and monoclonal Antibody Therapy in ANCA Positive Vasculitis: Experience in Four Cases," *Autoimmunity* 28(3):163-71 (1998).

M Kobayashi et al., "Immunohistochenical Analysis of Arterial Wall Cellular Infiltration in Buerger's Disease(Endoarteritis Obliterans)," *J. Vascular Surgery* 29(3):451-8 (Mar. 1999).

Y Goto et al., "Increased Production of B Cell Growth Factor (BCFG) in Sjorgen's Syndrome," *J. Autoimmunity* 9(4):545-50 (1996).

M Falcone et al., "B Lymphocytes Are Crucial Antigen-Presenting Cells in the Pathogenic Autoimmune Response to GAD65 Antigen in Nonobese Diabetic Mice," *J. Immunol.* 161(3):1163-8 (Aug. 1, 1998).

L Chatenoud et al., "Anti-CD3 Antibody induces Long-Term Remission of Overt Autoimmunity in Nonobese Diabetic Mice," *Proc. Natl. Acad. Sci.* (USA) 91(1):123-7 (Jan. 4, 1994).

Edwards, "Is Rheumatoid Factor Relevant?", Challenges in Rheumatoid Arthritis, Chapt. I, pp. 1-24 (HA Brid, ML Snaith eds. Jan. 3, 1999).

D Wendling et al., "A Randomized Double Blind, Placebo Controlled Multicenter Trial of Murine Anti-CD4 Monoclonal Antibody Therapy in Rheumatoid Arthritis," J. Rheumatology 25(8):1457-61 (Aug. 1998).

W Krenger et al., "Graft-versus-host disease and the Th1/Th2 paradigm," Immunol. Res. 15(1):50-73 (1996).

Business Wire, "IDEC Pharmaceuticals initiates phase III registration trial of IDEC-Y2B8 and Rituxan in the treatment of relapsed or refractory non-Hodgkin's lymphoma," pp. 1-2, Feb. 24, 2002.

DG Maloney et al., "Phase I clinical trial using escalating single-dose infusion of chimeric anti-CD20 monoclonal antibody (IDEC-C2B8) in patients with recurrent B-cell lymphoma," Blood 84:2457-66 (1994).

MJ Polyak & JP Deans, "Alanine-170 and proline-172 are critical determinants for extracellular CD20 epitopes; heterogeneity in the fine specificity of CD20 monoclonal antibodies is defined by additional requirements imposed by both amino acid, sequence and quaternary structure," Blood 99(9):3256-62 (2002).

HB Lowman, "Differential Activities in a Series of Humanized Anti-CD20 Antibodies," presented at IBC Antibody Engineering Conference, San Diego, CA, Dec. 2, 2003.

Statement by Randall M. Stevens, M.D., submitted in opposition proceedings involving EP1176981, one page (signed Sep. 3, 2008).

Second Statement by Dr. Penelope Ward, submitted in opposition proceedings involving EP1176981, pp. 1-2 (signed Sep. 3, 2008).

Statement by Dr. Urs Schleuniger, submitted in opposition proceedings involving EP1176981, pp. 1-2 (signed Sep. 3, 2008).

Second Declaration of Prof. Jonathan Charles Wright Edwards, submitted in opposition proceedings involving EP1176981, pp. 1-4 (signed Aug. 8, 2008).

Tzioufas, A.G., et al., "Sjögren's Syndrome: An Oligo-Monoclonal B Cell Process", *Clinical and Experimental Rheumatology*, 1990, 8(5), pp. 17-21.

Declaration of Catherine Cronin, submitted in opposition of EP1176981, pp. 1-3, with 2 page attachment (signed Mar. 5, 2008)

Declaration of Christian Jorgensen, submitted in opposition of EP1176981, pp. 1-2 (signed Mar. 6, 2008).

Declaration of Dennis Carson, submitted in opposition of EP1176981, pp. 1-2, with 2 page attachment (signed Feb. 25, 2008).

Declaration of Gabriel Panayi, submitted in opposition of EP1176981, pp. 1-3 (signed Feb. 27, 2008).

Declaration of Gillian Fernandez, submitted in opposition of EP1176981, pp. 1-3 (signed Mar. 3, 2008).

Declaration of Hani El-Gabalawy, submitted in opposition of E176981, pp. 1-2, Appendices A-C (signed Mar. 11, 2008).

Declaration of Jonathan Charles Wright Edwards, submitted in opposition of EP1176981, pp. 1-8, Appendices A-I (signed Feb. 27, 2008).

Declaration of Marion Cronin, submitted in opposition of EP1176981, pp. 1-2 (signed Mar. 3, 2008).

Houssiau, F.A., et al., "Immunotherapeutic Approaches of Rheumatic Disorders", *Acta Clinica Belgica*, 1998, 53(3), pp. 155-161.

Svensson, L., et al., "B cell-deficient mice do not develop type II collagen-induced arthritis (CIA)", *Clin. Exp. Immunol.*, 1998, vol. 111. No. 3, pp. 521-526.

Decision of the European Opposition Division related to EP1176981, including the decision (2 pages) and grounds for the decision (8 pages), Dec. 16, 2008.

The European Medicines Agency (EMEA) Summary of Mabthera Product Characteristics, pp. 1-80, obtained at http://www.emea.europa.eu/humandocs/PDFs/EPAR/Mabthera/H-165-PI-en.pdf (obtained Aug. 2007).

"Efficacy" print-out from www.rituxan.com, pp. 1-6 (printed Jul. 2007).

Declaration of Dr. Ronald van Vollenhoven, submitted in opposition proceedings involving EP1176981, pp. 1-11, with c.v. as Annex A (signed Jun. 20, 2008).

Declaration of Prof. Michael Weinblatt, submitted in opposition proceedings involving EP1176981, pp. 1-5, with c.v. (signed Jul. 8, 2008).

O'Dell, "The Treatment of Rheumatoid Arthritis in 1995: Results of a Survey," ACR Poster Session F, Abstract 1277 (Oct. 25, 1995).

Statement by Dr. Penelope Ward, submitted in opposition proceedings involving EP1176981, pp. 1-3, with c.v. (signed Jul. 8, 2008).

Statement by Prof. Paul Emery, submitted in opposition proceedings involving EP1176981, pp. 1-4, with c.v. as Exhibit 1 (signed Jul. 1, 2008).

The Fourth International Synovitis Workshop, Abstract of C. Berek & H.J. Kim, p. 13 (Dallas, TX, Apr. 21-25, 1999).

The Fourth International Synovitis Workshop, Abstract of Dennis Carson, p. 19 (Dallas, TX, Apr. 21-25, 1999).

The Merck Manual of Diagnosis and Therapy, pp. 416-423 ($17^{th}$ ed. 1999).

Bioworld Today, "'Reviewing the data' before continuing SmithKline holds up trials of RA drug in IDEC deal," Dec. 28, 1998, v9, i247 pNA.

Cash et al., "Drug Therapy," New Engl. J. Med. 330:1368-75 (1994).

De Vita et al., "Efficacy of Selective B Cell Blockade in the Treatment of Rheumatoid Arthritis," Arthritis & Rheumatism 46:2029-33 (2002).

Edwards, "Can IgG Rheumatoid Factors Explain Everything?," The 4th Ann. Int'l Synovitis Workshop, Programs & Abstracts, p. 23 (Dallas, Apr. 21-25, 1999).

Edwards, "The Case for Killing B Cells With Anti-CD20 in RA," Abstract R21, The Australia Rheumatology Association, 41st Ann. Scientific Conf., p. 53 (Sydney, May 24-27, 1998).

Edwards, et al., "B cell Depletion in Rheumatoid Arthritis," 6th Int'l Symposium on the Immunotherapy of the Rheumatic Diseases, pp. 1-8 (2002).

Edwards, "Sustained Improvement in Rheumatoid Arthritis Following a B Lymphocyte Depletion Protocol," Rheumatology, vol. 39(Abs. Supp. 1):89 (2000).

Ghetie et al., "Evaluation of ricin A chain-containing immunotoxins directed against CD19 and CD22 antigens on normal and malignant human B-cells as potential reagents for in vivo therapy," Cancer Research, 1988, pp. 2610-2617, vol. 48, No. 9.

Hekman et al., "Initial experience with treatment of human B cell lymphoma with anti-CD19 monoclonal antibody," Cancel Immunology Immunotherapy, 1991, pp. 364-372, vol. 32.

Hess et al., "Specificity of effector T lymphocytes in autologous graft-versus-host disease: role of the major histocompatibility complex class II invariant chain peptide," Blood, Mar. 1997, pp. 2203-2209, vol. 89, No. 6.

Hirano et al., "Excessive production of interleukin 6/B cell stimulatory factor-2 in rheumatoid arthritis," Eur. J. Immunol. 18:1797-1801 (1988).

Kaminski et al., "Radioimmunotherapy of B-cell lymphoma with [131I]anti-B1 (anti-CD20) antibody," The New England Journal of Medicine, 1993, pp. 459-465, vol. 329, No. 7.

Leung et al., "Chimerization of LL2, a rapidly internalizing antibody specific for B cell lymphoma," Hybridoma, 1994, pp. 469-476, vol. 13, No. 6.

Leung et al., "Construction and characterization of a humanized, internalizing, B-cell (CD22)-specific, leukemia/lymphoma antibody, LL2," Mol. Immunol. 1995, pp. 1413-1427, vol. 32, No. 17/18.

Longo, "Immunotherapy for Non-Hodgkin's Lymphoma," Current Opinion in Oncology, 1996, pp. 353-359, vol. 8, No. 5.

Maloney et al., "IDEC-C2B8: results of a phase I multiple-dose trial in patients with relapsed non-Hodgkin's lymphoma," J. Clin. Oncol. 15(10):3266-74 (May 1997).

Oxford Dictionary of Biochemistry and Molecular Biology, Oxford Univ. Press, Oxford, 1997, p. 77, col. 1.

Press et al., "Phase II Trial of 131 I-B1 (anti-CD20) Antibody Therapy with Autologous Stem Cell Transplantation for Relapsed B Cell Lymphomas," The Lancet, 1995, pp. 336-340, vol. 346, No. 8971.

Press et al., "Radiolabeled-Antibody Therapy of B-Cell Lymphoma with Autologous Bone Marrow Support," The New England Journal of Medicine, 1993, pp. 1219-1224, vol. 329, No. 17.

Shih et al., "Internalization and Intracellular Processing of Anti-B-Cell Lymphoma Monoclonal Antibody, LL2," Int. J. Cancer, 1994, pp. 538-545, vol. 56.

The Merck Manual of Diagnosis and Therapy (Seventh Edition, Beers et al., eds., Merck Research Laboratories, Whitehouse Station, NJ, 1999, Chapter 180, "Demyelinating Diseases," pp. 1474-1476.

"Biogen and IDEC Pharmaceuticals Complete Merger to Create New Biotechnology Industry Leader," Biogen IDEC press release, pp. 1-4 (Nov. 12, 2003).

Declaration of Gabriel Panayi submitted in opposition of EP1176981, p. 1-4, Appendices A-E (signed Aug. 24, 2006).

"Phase III Study Shows Rituxan Significantly Improves Symptoms in Patients with Rheumatoid Arthritis Who Inadequately Responded to Anti-TNF Therapies," Genentech press release (Apr. 5, 2005).

Product insert for Rituxan®, pp. 1-4 (patient information approval Feb. 28, 2006).

"Update on B Lymphocyte Depletion Therapy," http://web.archive.org/web/20001109083000/www.ucl.ac.uk/~regfjxe/B.htm, p. 1, internet excerpt cited in opposition of EP1176981 (printed Aug. 8, 2006).

Alamo et al., "Methotrexate in rheumatoid arthritis," Rev. Med. Chil. 1196(6):691-700 (1991); PMID 1844376; English language abstract only.

Fukai et al., "The role of costimulatory molecules B7-1 and B7-2 in mice with experimental autoimmune uveroretinitis," Graefes. Arc. Clin. Exp. Opthalmol. 237(11):928-933 (1999).

Gazzano-Santoro et al., "A non-radioactive complement-dependent cytotoxicity assay for anti-CD20 monoclonal antibody," J. Immunol. Methods 202:163-171 (1997).

Joosten et al., "Protection against cartilage and bone destruction by systemic interleukin-4 treatment in established murine type II collagen-induced arthritis," Arthritis Res. 1(1):81-91 (1999), available at <http://arthritis-research.com/26oct99/ar0101p03>.

Matsuura et al., "Effect of FTY720, a novel immunosuppressant, on adjuvant-induced arthritis in rats," Inflamm. Res. 49(8):404-410 (2000).

Ruderman et al., "Oral glucocorticoids have no impact on the efficacy or safety profile of rituximab in rheumatoid arthritis (RA) patients with inadequate response to TNF inhibitors(REFLEX study)," presented at The American College of Rheumatology Meeting; Nov. 10-15, 2006; Washington, DC. Abstract 454.

Schoeffel et al., "Elevated Expression of HLA-Class II Antigen Positive Peripheral Blood T Lymphocytes in Multiple Sclerosis Results of an 18 Month Longitudinal Study," Zeitschrift Fuer Klinische Medizin (Berlin) 46(12):918-21 (1991) (including English language abstract).

Smolen et al., "Efficacy and safety of leflunomide in active rheumatoid arthritis," Rheumatology 39(Suppl. 1):48-56 (2000).

Takahashi et al., "Functional interaction of the immunosuppressant mizorbine with the 14-3-3 protein," BBRC 274(1):87-92 (2000), doi:10.1006/bbrc.2000.3104.

Trepicchio et al., "The therapeutic utility of interleukin-11 in the treatment of inflammatory disease," Expert Opin. Investig. Drugs. 7(9):1501-1504 (1998).

Emery et al., "The Efficacy and Safety of Rituximab in Patients With Active Rhematoid Arthtritis Despite Methotrexate Treatment," Arthritis & Rheumatism 54(5): 1390-1400 (2006).

Kremer, "Safety, efficacy, and mortality in a long-term cohort of patients with rheumatoid arthritis taking methotrexate followup after a mean of 13.3 years," Arthritis & Rheum. 40(5): 984-5 (1997).

Kremer, "Combination therapy with biologic agents in rheumatoid arthritis: Perils and promise," Arthritis & Rheum. 41(9): 1548-1551 (1998).

Maini et al., "Therapeutic efficacy of multiple intravenous infusions of anti-tumor necrosis factor α monoclonal antibody combined with low-dose weekly methotrexate in rheumatoid arthritis," Arthritis & Rheum. 41(9): 1552-63 (1998).

Strand et al., "Differential patterns of response in patients. with rheumatoid arthritis following administration of an anti-CD5 Immunoconjugate," Clin. Exp. Rheumatol. 11(Suppl 8): S161-3 (1993).

UK IPO Register Entry for European Patent Application No. 00928991.9, pp. 1-2; dated Jan. 10, 2006; ADP No. 66354200001; obtained from Mewburn Ellis (Crown Copyright, UK Intellectual Property Office, 2008).

Weinblatt et al., "Low-dose methotrexate compared with Aranofin in adult rheumatoid arthritis—A thirty-six-week, double-blind trial," Arthritis & Rheum. 33(3): 330-8 (1990).

Weinblatt et al., "Longterm Prospective Study of Methotrexate in Rheumatoid Arthritis: Conclusion After 132 Months of Therapy," J. Rheumatol. 25: 238-42 (1998).

Weinblatt et al., "A trial of etanercept, a recombinant tumor mecrosis factor receptor:Fc fusion protein, in patients with rheumatoid arthritis receiving methotrexate," N. Engl. J. Med. 340(4): 253-9 (1999).

Bankhurst et al., "Predominance of T cells in the lymphocytic infiltrates of synovial tissues in rheumatoid arthritis," Arthritis and Rheumatism 19(3): 555-562 (1976).

Breedveld et al., "Editorial: T cells in rheumatoid arthritis," British Journal of Rheumatology 36(6): 617-619 (1997).

Cambridge et al., "Serologic Changes Following B Lymphocyte Depletion Therapy for Rheumatoid Arthritis," Arthritis and Rheumatism 48(8): 2146-54 (2003).

Chan et al., "A Novel Mouse with B Cells but Lacking Serum Antibody Reveals an Antibody-independent Role for B Cells in Murine Lupus," J. Exp. Med. 189(10): 1639-1647 (1999).

Choy et al., "Anti-CD4 monoclonal antibodies in rheumatoid arthritis," Springer Semin. Immunopathol. 20: 261-273 (1998).

Choy et al., "Monoclonal antibody therapy in rheumatoid arthritis," British Journal of Rheumatology 37: 484-490 (1998).

Dolhain et al., "Shift toward T lymphocytes with a T helper 1 cytokine-secretion profile in the joints of patients with rheumatoid arthritis," Arthritis and Rheumatism 39(12): 1961-1969 (1996).

Edwards & Cambridge, "Is rheumatoid arthritis a failure of B cell death in synovium?", Ann. Rheum. Dis. 54: 696-700 (1995).

Edwards et al., "Restricted expression of FcγRIII (CD16) in synovium and dermis: implications for tissue targeting in rheumatoid arthritis (RA)," Clin. Exp. Immunol. 108: 401-406 (1997).

Edwards et al., "Expression of molecules involved in B lymphocyte survival and differentiation by synovial fibroblasts," Clin. Exp. Immunol. 108: 407-414 (1997).

Emery et al., "Targeted therapies in rheumatoid arthritis: the need for action," Rheumatology 38: 911-912 (1999).

Hendrich et al., "Activation of CD16+ effector cells by Rheumatoid factor complex," Arthritis and Rheumatism 34(4): 423-431 (1991).

Kyburz et al., "Human Rheumatoid Factor Production Is Dependent on CD40 Signaling and Autoantigen," J. Immunol. 163: 3116-3122 (1999).

Manz et al, "Survival of long-lived plasma cells is independent of antigen," International Immunology 10(11): 1703-1711 (1998).

Matusmoto et al., "Arthritis Provoked by Linked T and B Cell Recognition of a Glycolytic Enzyme," Science 286: 1732-1735 (1999).

Pulendran et al., "Immunological tolerance in germinal centres," Immunology Today, 18(1): 27-32 (1997).

Roosnek & Lanzavecchia, "Efficient and Selective Presentation of Antigen-Antibody Complexes by Rheumatoid Factor B Cells," J. Exp. Med. 173:487-489 (1991).

Shlomchik et al., "The Role of B Cells in 1pr/lpr-induced Autoimmunity," J. Exp. Med. 180: 1295-1306 (1994).

Andersson, "Digital Image Analysis to Quantify Inflammation in Synovial Tissue," The Fourth International Synovitis Workshop, Collected Programs and Abstracts, Dallas, TX, Apr. 21-25, 1999, p. 11 (Scientific Frontiers, Inc. 1999).

Gabay et al., "Interleukin-1 Receptor Antagonist Isoforms in Collagen-Indiced Arthritis," The Fourth International Synovitis Workshop, Collected Programs and Abstracts, Dallas, TX, Apr. 21-25, 1999, p. 12 (Scientific Frontiers, Inc. 1999).

Berek & Kim, "Evidence for an Antigen*Driven Immune Response in the Chronically Inflamed Synovium," The Fourth International Synovitis Workshop, Collected Programs and Abstracts, Dallas, TX, Apr. 21-25, 1999, p. 13 (Scientific Frontiers, Inc. 1999).

Bresnihan, "Synovial Tissue Analysis in Clinical Stuaies," The Fourth International Synovitis Workshop, Collected Programs and Abstracts, Dallas, TX, Apr. 21-25, 1999, p. 15 (Scientific Frontiers, Inc. 1999).

Bridges, "Expression of RAG1 RAG2.1 and TdT in Rheumatoid Arthritis Synovia: Evidence for Receptor Revision of Immunoglobulin Light Chains," The Fourth International Synovitis Workshop, Collected Programs and Abstracts, Dallas, TX, Apr. 21-25, 1999, p. 16 (Scientific Frontiers, Inc. 1999).

Burkhardt et al., "Collagen Type II-Specific Autoantibodies in Chronic Inflammatory Joint Diseases," The Fourth International Synovitis Workshop, Collected Programs and Abstracts, Dallas, TX, Apr. 21-25, 1999, p. 17 (Scientific Frontiers, Inc. 1999).

Burmester et al., "Monocytes and Macrophages in Synovitis: Villains or Victims?" The Fourth International Synovitis Workshop, Collected Programs and Abstracts, Dallas, TX, Apr. 21-25, 1999, p. 18 (Scientific Frontiers, Inc. 1999).

Carson, "Role of Rheumatoid Factor B Cells in Normal and Pathologic Antigen Presentation," The Fourth International Synovitis Workshop, Collected Programs and Abstracts, Dallas, TX, Apr. 21-25, 1999, p. 19 (Scientific Frontiers, Inc. 1999).

Chiorazzi, "Synovial B Cells in Rheumatoid Arthritis: Clonal Expansion, Diversification, and Persistence," The Fourth International Synovitis Workshop, Collected Programs and Abstracts, Dallas, TX, Apr. 21-25, 1999, p. 20 (Scientific Frontiers, Inc. 1999).

Crofford, "The Role of COX-2 in Rheumatoid Arthritis Synovial Tissues," The Fourth International Synovitis Workshop, Collected Programs and Abstracts, Dallas, TX, Apr. 21-25, 1999, p. 21 (Scientific Frontiers, Inc. 1999).

Dayer, Interfacing With Inflammation During Cell-Cell Interaction, The Fourth International Synovitis Workshop, Collected Programs and Abstracts, Dallas, TX, Apr. 21-25, 1999, p. 22 (Scientific Frontiers, Inc. 1999).

Edwards, "Can IgG Rheumatoid Factors Explain Everything?" The Fourth International Synovitis Workshop, Collected Programs and Abstracts, Dallas, TX, Apr. 21-25, 1999, p. 23. (Scientific Frontiers, Inc. 1999).

Lee et al., "Predictors of Early Bone Erosion in Patients With Synovitis of Recent Onset,"The Fourth International Synovitis Workshop, Collected Programs and Abstracts, Dallas, TX, Apr. 21-25, 1999, p. 24 (Scientific Frontiers, Inc. 1999).

Emery, "Assessment of Innovative Therapies: A Mode-of-Action Approach," The Fourth International Synovitis Workshop, Collected Programs and Abstracts, Dallas, TX, Apr. 21- 25, 1999, p. 25 (Scientific Frontiers, Inc. 1999).

Evans, "Lessons Learned From Gene Therapy Approaches," The Fourth International Synovitis Workshop, Collected Programs and Abstracts, Dallas, TX, Apr. 21-25, 1999, p. 26 (Scientific Frontiers, Inc. 1999).

Feldmann et al., "Adenovirus as a Useful Probe for Defining Signalling Pathways in Macrophages and Synovial Cell Cultures," The Fourth International Synovitis Workshop, Collected Programs and Abstracts, Dallas, TX, Apr. 21-25, 1999, p. 27 (Scientific Frontiers, Inc. 1999).

Firestein, "Life and Death in the Synovium," The Fourth International Synovitis Workshop, Collected Programs and Abstracts, Dallas, TX, Apr. 21-25, 1999, p. 28 (Scientific Frontiers, Inc. 1999).

Gay et al., "Activation of Synovial Fibroblasts in Rheumatoid Arthritis," The Fourth International Synovitis Workshop, Collected Programs and Abstracts, Dallas, TX, Apr. 21-25, 1999, p. 29 (Scientific Frontiers, Inc. 1999).

Goronzy, "T Cell Homeostasis and Repertoire Contraction in Rheumatoid Arthritis," The Fourth International Synovitis Workshop, Collected Programs and Abstracts, Dallas, TX, Apr. 21-25, 1999, p. 30 (Scientific Frontiers, Inc. 1999).

Gravallese et al., "Histopathology of Bone Erosions in Rheumatoid Arthritis," The Fourth International Synnovitis Workshop, Collected Programs and Abstracts, Dallas, TX, Apr. 21-25, 1999, p. 31 (Scientific Frontiers, Inc. 1999).

Hirohata & Sakibara, "Synovial Histopathology in Early Rheumatoid Arthritis," The Fourth International Synovitis Workshop, Collected Programs and Abstracts, Dallas, TX, Apr. 21-25, 1999, p. 32 (Scientific Frontiers, Inc. 1999).

Homdahl, "Genetic Studies in Experimental Arthritis," The Fourth International Synovitis Workshop, Collected Programs and Abstracts, Dallas, TX, Apr. 21-25, 1999, p. 33 (Scientific Frontiers, Inc. 1999).

Isakson et al., "Peripheral VS. Central Role of COX-2 in Inflammation," The Fourth International Synovitis Workshop, Collected Programs and Abstracts, Dallas, TX, Apr. 21-25, 1999, p. 34 (Scientific Frontiers, Inc. 1999).

Jorgensen et al., "New Vectors and New Targets for Gene Therapy in Rheumatoid Arthritis," The Fourth International Synovitis Workshop, Collected Programs and Abstracts, Dallas, TX, Apr. 21-25, 1999, p. 35 (Scientific Frontiers, Inc. 1999).

Kalden et al., "Obstacles to Anti-CD4 Therapy in Rheumatoid Arthritis," The Fourth International Synovitis Workshop, Collected Programs and Abstracts, Dallas, TX, Apr. 21-25, 1999, p. 36 (Scientific Frontiers, Inc. 1999).

Kock, "Chemokines in Rheumatoid Arthritis," The Fourth International Synovitis Workshop, Collected Programs and Abstracts, Dallas, TX, Apr. 21-25, 1999, p. 38 (Scientific Frontiers, Inc. 1999).

Krane, "Overview: Destruction of the Extracellular Matrix in Rheumatoid Arthritis," The Fourth International Synovitis Workshop, Collected Programs and Abstracts, Dallas, TX, Apr. 21-25, 1999, p. 39 (Scientific Frontiers, Inc. 1999).

Loetscher, "Chemokines and Chemokine Receptors in Lymphocyte Traffic," The Fourth International Synovitis Workshop, Collected Programs and Abstracts, Dallas, TX, Apr. 21-25, 1999, p. 40 (Scientific Frontiers, Inc. 1999).

Maini et al., "The Role of TNF-α in the Pathogenesis of Rheumatoid Synovitis," The Fourth International Synnovitis Workshop, Collected Programs and Abstracts, Dallas, TX, Apr. 21-25, 1999, p. 41 (Scientific Frontiers, Inc. 1999).

McInnes, "T Cell Maturation in Inflammatory Synovitis," The Fourth International Synovitis Workshop, Collected Programs and Abstracts, Dallas, TX, Apr. 21-25, 1999, p. 42 (Scientific Frontiers, Inc. 1999).

Menard, "Pathogenic Implication of the RA-Specific Sa and RA-Associated Calpastatin Autoimmune Systems in Rheumatoid Synovitis," The Fourth International Synovitis Workshop, Collected Programs and Abstracts, Dallas, TX, Apr. 21-25, 1999, p. 43 (Scientific Frontiers, Inc. 1999).

Miossec, "Contribution of T Cell Subsets to Joint Degradation," The Fourth International Synovitis Workshop, Collected Programs and Abstracts, Dallas, TX, Apr. 21-25, 1999, p. 43 (Scientific Frontiers, Inc. 1999).

Moreland, "Etanercept for Treating Rheumatoid Arthritis," The Fourth International Synovitis Workshop, Collected Programs and Abstracts, Dallas, TX, Apr. 21-25, 1999, p. 44 (Scientific Frontiers, Inc. 1999).

Natvig et al., "Significance of Autoantibodies in Health and disease," The Fourth International Synovitis Workshop, Collected Programs and Abstracts, Dallas, TX, Apr. 21-25, 1999, p. 45 (Scientific Frontiers, Inc. 1999).

Nepom, "Genetics of Rheumatoid Arthritis," The Fourth International Synovitis Workshop, Collected Programs and Abstracts, Dallas, TX, Apr. 21-25, 1999, p. 46 (Scientific Frontiers, Inc. 1999).

Nishioka, "Apoptosis in Rheumatoid Synoviocytes," The Fourth International Synovitis Workshop, Collected Programs and Abstracts, Dallas, TX, Apr. 21-25, 1999, p. 48 (Scientific Frontiers, Inc. 1999).

The Fourth International Synovitis Workshop, Collected Programs and Abstracts, Dallas, TX, Apr. 21-25, 1999, p. 48(Scientific Frontiers, Inc. 1999).

Ochi, "Biologic Aspects of Nurse-Like Cells Found in Bone Marrow and Synovial Tissue of Rheumatoid Arthritis Patients," The Fourth International Synovitis Workshop, Collected Programs and Abstracts, Dallas, TX, Apr. 21-25, 1999, p. 49 (Scientific Frontiers, Inc. 1999).

O'Dell, "Combination Therapy," The Fourth International Synovitis Workshop, Collected Programs and Abstracts, Dallas, TX, Apr. 21-25, 1999, p. 50 (Scientific Frontiers, Inc. 1999).

Panayi et al., "The „78 Putative Rheumatoid Arthritis T Cell Autoantigen," The Fourth International Synovitis Workshop, Collected Programs and Abstracts, Dallas, TX, Apr. 21-25, 1999, p. 51 (Scientific Frontiers, Inc. 1999).

Skapenko et al., "Altered T Cell Differentiation in Patients with Early Rheumatoid Arthritis," The Fourth International Synovitis Workshop, Collected Programs and Abstracts, Dallas, TX, Apr. 21-25, 1999, p. 52 (Scientific Frontiers, Inc. 1999).

Steiner, "Is the Spliceosome an Autoimmune Target in Rheumatoid Arthritis?" The Fourth International Synovitis Workshop, Collected Programs and Abstracts, Dallas, TX, Apr. 21-25, 1999, p. 53 (Scientific Frontiers, Inc. 1999).

Tak, "Synovial Tissue Response to Treatment: The Effects of IFN-β Treatment in Rheumatoid Arthritis Patients," The Fourth International Synovitis Workshop, Collected Programs and Abstracts, Dallas, TX, Apr. 21-25, 1999, p. 54 (Scientific Frontiers, Inc. 1999).

Tetlow & Woolley, "Effect of 1α,25 Oihydroxvitamin D3 on Matrix Metalloproteinase and Prostaglandin $E_2$ Production by Cells of the Rheumatoid Lesion," The Fourth International Synovitis Workshop, Collected Programs and Abstracts, Dallas, TX, Apr. 21-25, 1999, p. 55 (Scientific Frontiers, Inc. 1999).

Thomas et al., "Dendritic Cells: What Is Their True Role in Rheumatoid Arthritis?" The Fourth International Synovitis Workshop, Collected Programs and Abstracts, Dallas, TX, Apr. 21-25, 1999, p. 56 (Scientific Frontiers, Inc. 1999).

Tyndall, "Stem Cell Transplantation in the Treatment of Rheumatoid Arthritis and Other Autoimmune Diseases," The Fourth International Synovitis Workshop, Collected Programs and Abstracts, Dallas, TX, Apr. 21-25, 1999, p. 57-58 (Scientific Frontiers, Inc. 1999).

van de Putte, "Rheumatoid Arthritis Is a Lining Cell Disease: An Evolving Concept," The Fourth International Synovitis Workshop, Collected Programs and Abstracts, Dallas, TX, Apr. 21-25, 1999, p. 59 (Scientific Frontiers, Inc. 1999).

van den Berg, "Role of Cytokines in Cartilage Destruction in Experimental Arthritis," The Fourth International Synovitis Workshop, Collected Programs and Abstracts, Dallas, TX, Apr. 21-25, 1999, p. 60 (Scientific Frontiers, Inc. 1999).

van Venrooij, "Citrullinated Peptides as a Substrate for the Detection of Rheumatoid Arthritis-Specific Autoantibodies," The Fourth International Synovitis Workshop, Collected Programs and Abstracts, Dallas, TX, Apr. 21-25, 1999, p. 61 (Scientific Frontiers, Inc. 1999).

Wassmuth, "Immunogenetic Aspects of Disease Progression in Rheumatoid Arthritis," The Fourth International Synovitis Workshop, Collected Programs and Abstracts, Dallas, TX, Apr. 21-25, 1999, p. 62 (Scientific Frontiers, Inc. 1999).

Weyland, "Rheumatoid Arthritis: A Polygenic Disease With Multiple Phenotypes," The Fourth International Synovitis Workshop, Collected Programs and Abstracts, Dallas, TX, Apr. 21-25, 1999, p. 63 (Scientific Frontiers, Inc. 1999).

Winchester, "Fibroblastoia Synoviocytes: Their Intrinsic and Disease-Modified Phenotype as Revealea by a Differential Subtraction Library Approach," The Fourth International Synovitis Workshop, Collected Programs and Abstracts, Dallas, TX, Apr. 21-25, 1999, p. 64 (Scientific Frontiers, Inc. 1999).

Woolley & Tetlow, "Mast Cells and the Rheumatoid Lesion," The Fourth International Synovitis Workshop, Collected Programs and Abstracts, Dallas, TX, Apr. 21-25, 1999, p. 65 (Scientific Frontiers, Inc. 1999).

Youssef, "The Effects of "Pulse" Corticosteroids on Mediators of Inflammation and Joint Damage in the Rheumatoid Synovium," The Fourth International Synovitis Workshop, Collected Programs and Abstracts, Dallas, TX, Apr. 21-25, 1999, p. 66 (Scientific Frontiers, Inc. 1999).

Dorner et al., "Initial clinical trial of epratuzumab (humanized anti-CD22 antibody) for immunotherapy of systemic lupus erythematosus," Arthritis Res. & Therapy 2006; 8(3):R74, electronic publication, Apr. 21, 2006, pp. 1-11; available online at http://arthritis-research.com/content/8/3/R74.

Jacobi et al., "Differential effects of epratuzumab on peripheral blood B cells of SLE patients versus normal controls," Ann. Rheum. Dis., electronic publication, Aug. 2, 2007, pp. 1-14, Figures 1-5; available at http://ard.bmj.com/cgi/content/abstract/ard.2007.075762v1.

Steinfeld et al., "Epratuzumab (humanised anti-CD22 antibody) in primary Sjögren's syndrome: an open-label phase I/II study," Arthritis Res. & Therapy 2006; 8(4):R129, electronic publication, Jul. 20, 2006, pp. 1-11; previously available online at http://arthritis-research.com/content18/4/R129.

Carson et al., "Rheumatoid Factor and Immune Networks," Ann. Rev. Immunol. 5:109-26 (1987).

Gottenberg, "Tolerance and short term efficacy of rituximab in 43 patients with systemic autoimmune diseases," Ann. Rheum. Dis. 64:913-920 (2005), downloaded May 10, 2007.

Harris & Vaughan, "Transfusion Studies in Rheumatoid Arthritis," Arthritis and Rheumatism 4:47-55 (1961).

Higashida, "Safety and Efficacy of Rituximab in Patients with Rheumatoid Arthritis Refractory to Disease Modifying Antirheumatic Drugs and Anti-Tumor Necrosis Factor-α Treatment," J. Rheumatol. 32(11):2109-2115 (2005).

Kavanaugh, "An overview of immunomudulatory intervention in rheumatoid arthritis," Drugs of Today 35(4-5):275-286 (1999).

Kneitz et al., "Effective B Cell Depletion with Rituximab in the Treatment of Autoimmune Diseases," Immunbiology 206:519-527 (2002).

Kneitz et al., "Improvement of refractory rheumatoid arthritis after depletion of B cells," Scand. J. Rheumatol. 33:82-86 (2004).

Panayi, "The pathogenesis of rheumatoid arthritis: From molecules to the whole patient," Br. J. Rheumatol. 32:533-536 (1993).

Waaler, "On the occurrence of a factor in human serum activating the specific agglutination of sheep blood corpuscles," ActaPathol. Microbiol. Scan. 17:172-188 (1940).

Derwent Information Ltd., "IDdb3" report, pp. 1-22, cited in opposition of EP1176981 (Aug. 23, 2006)

Definition of "Body Surface Area" obtained online from www.medterms.com, pp. 1-2 (printed Aug. 24, 2006); available online at http://www.medterms.com/script/main/art.asp?articlekey=39851.

Edwards & Cambridge Cure"Rheumatoid Arthritis and Autoimmunity: Causes and Possible Cure?", Online reference, pp. 1-11 (printed Aug. 8, 2006); previously available online at http://web.archive.org/web/19991009084050/www.ucl.ac.uki~regfixe/.

Edwards & Cambridge, "Sustained Improvement in Rheumatoid Arthritis following B Lymphocyte Depletion Protocol: in Rheumatoid Arthritis and Autoimmunity: A new approach to their cause and how long term cure might be achieved," Online reference, pp. 1-7 (printed Jul. 21, 2006); previously available online at http://www.infotech.demon.co.uk/regfixe.htm.

Plater-Zyberk et al., "CD5+ in Theumatoid Arthritis," Ann. N.Y. Acad. Sci. 651: 540-550 (1992).

Keystone, "Abandoned therapies and unpublished trials in rheumatoid arthritis," Current Opinion in Rheumatology 15: 253-258 (2003).

Chustecka, "Rituximab in RA: 'we should aim for permanent remission,'" Medscape Medical News, pp. 1-4 (Jun. 16, 2004); printed Aug. 8, 2008; available at <http://www.medscape.com/viewarticle/537826>.

Alawyn IPJ, Xu Y, Basker M, Wu C, Buhler L, Lambrigts D, et al. Effects of Specific Anti-B and/or Anti-Plasma Cell Immunotherapy on Antibody Production in Baboons: Depletion of CD20- and CD22-Positive B Cells Does Not Result in Significantly Reduced Production of Anti-Gal Antibody. Xenotransplantation 2001; 8:157-171.

Aranda JM, Scornik JC, Normann SJ, Lottenberg R, Schofield RS, Pauly DF, et al. Anti-CD20 Monoclonal Antibody (Rituximab) Therapy for Acute Cardiac Humoral Rejection: A Case Report. Transplantation 2002; 73:907-910.

Agarwal A, Vieira C, Book B, Fineberg N, Sidner R, Ochs H, et al. Rituximab, Anti-CD20 Inhibits a Human in Vivo Primary and Secondary Antibody Response to Bacteriophage PhiX174. Blood 2001; 98:608a.

Agarwal A, Vieira CA, Book BK, Zeni T, Sidner RA, Fineberg NA, et al. Effect of Rituximab on Natural Antibodies in Pre-Transplant Patients. American Journal Transplant 2002; 2 (Suppl. 3):345.

Garrett HE, Groshart K, Duvall-Seaman D, Combs D, Suggs R. Treatment of Humoral Rejection with Rituximab. Ann. Thoracic Surgeon 2002; 74:1240-1242.

Gloor JM, DeGoey SR, Pineda AA, Moore SB, Prieto M, Nyberg SL, et al. Overcoming a Positive Crossmatch in Living-Donor Kidney Transplantation. American Journal Transplantation 2003; 3:1017-1023.

Monteiro I, McLoughlin LM, Fisher A, de la Torre AN, Koneru B. Rituximab with Plasmapheresis and Splenectomy in ABO-Incompatible Liver Transplantation. Transplantation 2003; 76:1648-1649.

Pierson RN, Loyd Je, Goodwin A, Majors D, Dummer JS, Mohacsi P, et al. Successful Management of an ABO-Mismatched Lung Allograft Using Antigen-Specific Immunoadsorption, Complement Inhibition, and Immunomodulatory Therapy. Transplantation 2002; 74:79-84.

Sammartino C, Pham T, Panaro F, Bogetti D, Jarzembowski T, Sankary H, et al. Successful Simultaneous Pancreas Kidney Transplantation from Living-Related Donor Against Positive Cross-Match. American Journal Transplantation 2004; 4:140-143.

Sidner RA, Book BK, Agarwal A, Bearden CM, Vieira CA, Pescovitz MD. Rituximab for Reduction of HLA Antibodies in Patients Awaiting Renal Transplantation: Pattern of B Cell Recovery. FASEB J 2003; 17:C113.

Tyden G, Kumlien G, Fehrman I. Successful ABO-Incompatible Kidney Transplantations without Splenectomy Using Antigen-Specific Immunoadsorption and Rituximab. Transplantation 2003; 76:730-731.

Vieira CA, Agarwal A, Book BK, Sidner RA, Zeni T, Gebel HM, et al. Rituxan for Reduction of Anti-HLA Antibodies in Patients Awaiting Renal Transplantation. American Journal Transplantation 2002; 2:356.

Becker YT, Becker BN, Knechtle SJ, Odorico JS, D'Alessandro AM, Pirsch JD, Sollinger HW. Treatment of Steroid Resistant Rejection with a Novel Anti-B-cell Preparation, Rituximab. Transplantation 2000; 69 (8 Suppl.): S362.

Essell JH, Broun ER, Sigmund D, Tierney C, Devoe M, Heying K, et al. Treatment of Refractory Chronic Graft-vs-Host Disease with Infliximab. Procedure American Society Clinical Oncology 2003; 22:836.

McGuirk J, Dix S, Belt R. Rituximab and Immune Modulation Post Unrelated Donor Transplant as Treatment for Refractory Burkitt's-like Lymphoma. Blood 2000; 96 (Suppl 2):242b.

Ratanatharathorn V, Ayash L, Lazarus HM, Fu J, Uberti JP. Chronic Graft-Versus-Host Disease. Bone Marrow Transplant 2001; 28:121-129.

Ratanatharathorn V, Carson E, Reynolds C, Ayash LJ, Levine J, Yanik G, et al. Anti-CD20 Chimeric Monoclonal Antibody Treatment of Refractory Immune-Mediated Thrombocytopenia in a Patient with Chronic Graft-Versus-Host Disease, Ann Intern Med 2000; 133:275-279.

Ratanatharathorn V, Bociek RG, Pavletic SZ, Lynch JC, Ferrara JL, Uberti JP. Prior Therapy With Anti-CD20 Chimeric Antibody (Rituximab) May Decrease the Risk of Acute Graft-Versus-Host Disease (GVHD) in Patients with Non-Hodgkin's Lymphoma Receiving Allogeneic Stem Cell Transplantation. Blood 2000; 96:391a.

Szabolcs P, Reese M, Yancey K, Hall R, Joanne K. Combination Treatment of Bullous Skin GHVD With Anti-CD20 and Anti-CD25 Antibodies. Blood 2000; 96 (Suppl. 2):350b.

Thomson J, Vassiliou G, Veys P, Redmill B, Edelsten C. Epstein-Barr Virus Dacryoadenitis as a Complication of Bone Marrow Transplant in a Child with Combined Immunodeficiency. Eye 2001; 15:815-816.

Sawada T, Fuchinoue S, Teraoka S. Successful A1-to-0 ABO-Incompatible Kidney Transplantation After a Preconditioning Regimen Consisting of Anti-CD20 Monoclonal Antibody Infusions, Splenectomy, and Double-filtration Plasmapheresis. Transplantation 2002; 74:1207-1210.

Pulsczynski, Stanislaw, Antibody-induced Modulaton and Intracellular Transport of CD10 and CD19 Antigens in Human Malignant B Cells, Leukemia and Lymphoma, vol. 15, pp. 243-252.

Schadlow M.B., et al., Using Rituximab (Anti-CD20 Antibody) In A Patient With Paraneoplastic Pemphigus, J Drugs Dermatol 2003: 2(5): 564-567.

Penglis et al., "HLA DR4: A Link Between Rheumatoid Arthritis and Cat Exposure," Australian and New Zealand Journal of Medicine—The Journal of Internal Medicine published by the Royal Australasian College of Physicians, (abstract only) 28(5):734 (Oct. 1998).

Moreland et al., "Double-blind, placebo-controlled multicenter trial using chimeric monoclonal anti-CD4 antibody, cM-T412, in rheumatoid arthritis patients receiving concomitant methotrexate," Arthritis & Rheum. 38(11): 1581-8 (1995).

Edwards, J.C.W. (1998). Rheumatoid Arthritis—The Synovium. In: J.H. Klippel & P.A. Dieppe (Eds.) Rheumatology, Second Edition, (Chapter 6, pp. 6.1-6.8). Philadelphia, PA: Mosby Pub.

Weintraub, "Genentech's Gamble—Behind the biotech pioneer's quest to conquer autoimmune disease," Business Week, Dec. 17, 2007, pp. 44-48.

Breedveld, "Redox Balance Alterations and Hyporesponsiveness of Synovial T Cells in Rheumatoid Arthritis," The Fourth International Synovitis Workshop, Collected Programs and Abstracts, Dallas, TX, Apr. 21-25, 1999, p. 14 (Scientific Frontiers, Inc. 1999).

Cohen et al. For the REFLEX Trial Group, "Rituximab for Rheumatoid Arthritis Refractory to Anti-Tumor Necrosis Factor Therapy—Results of a Multicenter, Randomized, Double-Blind, Placebo-Controlled, Phase III Trial Evaluating Primary Efficacy and Safety at Twenty-Four Weeks," Arthritis and Rheumatism, 54(9):2793-2806 (Sep. 2006).

Matthews, "Breakthrough as scientists discover cure for arthritis," [online] Telegraph News UK (2000) [retrieved again on Apr. 9, 2010]. Retrieved from www.multsclerosis.org/news/Oct2000/ArthritisBreakthrough.html, pp. 1-2.

[unknown author] "New hope for people with rheumatoid arthritis?," [online], Arthritic Research Campaign, UK released Nov. 2000 [retrieved again on May 14, 2010]. Retrieved from web.archive.org/web/20070202073812/http://www.arc.org.uk/newsviews/press/nov2000/newhope.htm, pp. 1-2.

The Merck Index—An Encyclopedia of Chemicals, Drugs, and Biologicals, 12$^{th}$ Edition, Budavari S. et al., Eds.; Merck & Co.: Whitehouse Station, NJ, 1996; entry 6065 at p. 1025 ("Methotrexate").

"Highlights of Prescribing Information," U.S. BL 103705/5297 Amendment: Rituximab-Genentech, Inc., pp. 1-31, Regional (RA):Rituxan Final (Oct. 2009).

* cited by examiner

TREATMENT OF AUTOIMMUNE DISEASES

RELATED APPLICATIONS

This application is a non-provisional application filed under 37 CFR 1.53(b)(1), claiming priority under 35 USC 119(e) to provisional application Nos. 60/133,018, filed May 7, 1999 and 60/139,621, filed Jun. 17, 1999, the contents of which are incorporated herein by reference.

FIELD OF THE INVENTION

The present invention concerns treatment of autoimmune diseases with antagonists which bind to B cell surface markers, such as CD19 or CD20.

BACKGROUND OF THE INVENTION

Lymphocytes are one of many types of white blood cells produced in the bone marrow during the process of hematopoiesis. There are two major populations of lymphocytes: B lymphocytes (B cells) and T lymphocytes (T cells). The lymphocytes of particular interest herein are B cells.

B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody but instead produce the antibody in a form that can be secreted. Secreted antibodies are the major effector molecule of humoral immunity.

The CD20 antigen (also called human B-lymphocyte-restricted differentiation antigen, Bp35) is a hydrophobic transmembrane protein with a molecular weight of approximately 35 kD located on pre-B and mature B lymphocytes (Valentine et al. *J. Biol. Chem.* 264(19):11282-11287 (1989); and Einfeld et al. *EMBO J.* 7(3):711-717 (1988)). The antigen is also expressed on greater than 90% of B cell non-Hodgkin's lymphomas (NHL) (Anderson et al. *Blood* 63(6):1424-1433 (1984)), but is not found on hematopoietic stem cells, pro-B cells, normal plasma cells or other normal tissues (Tedder et al. *J. Immunol.* 135(2):973-979 (1985)). CD20 regulates an early step(s) in the activation process for cell cycle initiation and differentiation (Tedder et al., supra) and possibly functions as a calcium ion channel (Tedder et al. *J. Cell. Biochem.* 14D:195 (1990)).

Given the expression of CD20 in B cell lymphomas, this antigen can serve as a candidate for "targeting" of such lymphomas. In essence, such targeting can be generalized as follows: antibodies specific to the CD20 surface antigen of B cells are administered to a patient. These anti-CD20 antibodies specifically bind to the CD20 antigen of (ostensibly) both normal and malignant B cells; the antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered" to the neoplastic B cells. Irrespective of the approach, a primary goal is to destroy the tumor; the specific approach can be determined by the particular anti-CD20 antibody which is utilized and, thus, the available approaches to targeting the CD20 antigen can vary considerably.

CD19 is another antigen that is expressed on the surface of cells of the B lineage. Like CD20, CD19 is found on cells throughout differentiation of the lineage from the stem cell stage up to a point just prior to terminal differentiation into plasma cells (Nadler, L. *Lymphocyte Typing II* 2: 3-37 and Appendix, Renling et al. eds. (1986) by Springer Verlag). Unlike CD20 however, antibody binding to CD19 causes internalization of the CD19 antigen. CD19 antigen is identified by the HD237-CD19 antibody (also called the "B4" antibody) (Kiesel et al. *Leukemia Research II*, 12: 1119 (1987)), among others. The CD19 antigen is present on 4-8% of peripheral blood mononuclear cells and on greater than 90% of B cells isolated from peripheral blood, spleen, lymph node or tonsil. CD19 is not detected on peripheral blood T cells, monocytes or granulocytes. Virtually all non-T cell acute lymphoblastic leukemias (ALL), B cell chronic lymphocytic leukemias (CLL) and B cell lymphomas express CD19 detectable by the antibody B4 (Nadler et al. *J. Immunol.* 131:244 (1983); and Nadler et al. in *Progress in Hematology* Vol. XII pp. 187-206. Brown, E. ed. (1981) by Grune & Stratton, Inc).

Additional antibodies which recognize differentiation stage-specific antigens expressed by cells of the B cell lineage have been identified. Among these are the B2 antibody directed against the CD21 antigen; B3 antibody directed against the CD22 antigen; and the J5 antibody directed against the CD10 antigen (also called CALLA). See U.S. Pat. No. 5,595,721 issued Jan. 21, 1997 (Kaminski et al.).

The rituximab (RITUXAN®) antibody is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.). RITUXAN® is indicated for the treatment of patients with relapsed or refractory low-grade or follicular, CD20 positive, B cell non-Hodgkin's lymphoma. In vitro mechanism of action studies have demonstrated that RITUXAN® binds human complement and lyses lymphoid B cell lines through complement-dependent cytotoxicity (CDC) (Reff et al. *Blood* 83(2):435-445 (1994)). Additionally, it has significant activity in assays for antibody-dependent cellular cytotoxicity (ADCC). More recently, RITUXAN® has been shown to have anti-proliferative effects in tritiated thymidine incorporation assays and to induce apoptosis directly, while other anti-CD19 and CD20 antibodies do not (Maloney et al. *Blood* 88(10):637a (1996)). Synergy between RITUXAN® and chemotherapies and toxins has also been observed experimentally. In particular, RITUXAN® sensitizes drug-resistant human B cell lymphoma cell lines to the cytotoxic effects of doxorubicin, CDDP, VP-16, diphtheria toxin and ricin (Demidem et al. *Cancer Chemotherapy & Radiopharmaceuticals* 12(3):177-186 (1997)). In vivo preclinical studies have shown that RITUXAN® depletes B cells from the peripheral blood, lymph nodes, and bone marrow of cynomolgus monkeys, presumably through complement and cell-mediated processes (Reff et al. *Blood* 83(2):435-445 (1994)).

SUMMARY OF THE INVENTION

The present invention provides, in a first aspect, a method of treating an autoimmune disease in a mammal comprising administering to the mammal a therapeutically effective amount of an antagonist which binds to a B cell surface marker.

In a further aspect, the present invention pertains to an article of manufacture comprising a container and a composition contained therein, wherein the composition comprises an antagonist which binds to a B cell surface marker, and further comprising a package insert instructing the user of the composition to treat a patient having or predisposed to an autoimmune disease.

DETAILED DESCRIPTION OF THE PREFERRED EMBODIMENTS

I. Definitions

A "B cell surface marker" herein is an antigen expressed on the surface of a B cell which can be targeted with an antagonist which binds thereto. Exemplary B cell surface markers include the CD10, CD19, CD20, CD21, CD22, CD23, CD24, CD37, CD53, CD72, CD73, CD74, CDw75, CDw76, CD77, CDw78, CD79a, CD79b, CD80, CD81, CD82, CD83, CDw84, CD85 and CD86 leukocyte surface markers. The B cell surface marker of particular interest is preferentially expressed on B cells compared to other non-B cell tissues of a mammal and may be expressed on both precursor B cells and mature B cells. In one embodiment, the marker is one, like CD20 or CD19, which is found on B cells throughout differentiation of the lineage from the stem cell stage up to a point just prior to terminal differentiation into plasma cells. The preferred B cell surface markers herein are CD19 and CD20.

The "$CD_{20}$" antigen is a ~35 kDa, non-glycosylated phosphoprotein found on the surface of greater than 90% of B cells from peripheral blood or lymphoid organs. CD20 is expressed during early pre-B cell development and remains until plasma cell differentiation. CD20 is present on both normal B cells as well as malignant B cells. Other names for CD20 in the literature include "B-lymphocyte-restricted antigen" and "Bp35". The CD20 antigen is described in Clark et al. *PNAS (USA)* 82:1766 (1985), for example.

The "CD19" antigen refers to a ~90 kDa antigen identified, for example, by the HD237-CD19 or B4 antibody (Kiesel et al. *Leukemia Research II*, 12: 1119 (1987)). Like CD20, CD19 is found on cells throughout differentiation of the lineage from the stem cell stage up to a point just prior to terminal differentiation into plasma cells. Binding of an antagonist to CD19 may cause internalization of the CD19 antigen.

An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc.

An "antagonist" is a molecule which, upon binding to a B cell surface marker, destroys or depletes B cells in a mammal and/or interferes with one or more B cell functions, e.g. by reducing or preventing a humoral response elicited by the B cell. The antagonist preferably is able to deplete B cells (i.e. reduce circulating B cell levels) in a mammal treated therewith. Such depletion may be achieved via various mechanisms such antibody-dependent cell-mediated cytotoxicity (ADCC) and/or complement dependent cytotoxicity (CDC), inhibition of B cell proliferation and/or induction of B cell death (e.g. via apoptosis). Antagonists included within the scope of the present invention include antibodies, synthetic or native sequence peptides and small molecule antagonists which bind to the B cell marker, optionally conjugated with or fused to a cytotoxic agent. The preferred antagonist comprises an antibody.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and carry out ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Complement dependent cytotoxicity" or "CDC" refer to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Growth inhibitory" antagonists are those which prevent or reduce proliferation of a cell expressing an antigen to which the antagonist binds. For example, the antagonist may prevent or reduce proliferation of B cells in vitro and/or in vivo.

Antagonists which "induce apoptosis" are those which induce programmed cell death, e.g. of a B cell, as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

The term "antibody" herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the (3-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The term "hypervariable region" when used herein refers to the amino acid residues of an antibody which are responsible for antigen-binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196: 901-917 (1987)). "Framework" or "FR" residues are those variable domain residues other than the hypervariable region residues as herein defined.

An antagonist "which binds" an antigen of interest, e.g. a B cell surface marker, is one capable of binding that antigen with sufficient affinity and/or avidity such that the antagonist is useful as a therapeutic agent for targeting a cell expressing the antigen.

Examples of antibodies which bind the CD20 antigen include: "C2B8" which is now called "rituximab" ("RITUXAN®") (U.S. Pat. No. 5,736,137, expressly incorporated herein by reference); the yttrium-[90]-labeled 2B8 murine antibody designated "Y2B8" (U.S. Pat. No. 5,736,137, expressly incorporated herein by reference); murine IgG2a "B1" optionally labeled with $^{131}$I to generate the "$^{131}$I-B1" antibody (BEXXAR™) (U.S. Pat. No. 5,595,721, expressly incorporated herein by reference); murine monoclonal antibody "1F5" (Press et al. *Blood* 69(2):584-591 (1987)); "chimeric 2H7" antibody (U.S. Pat. No. 5,677,180, expressly incorporated herein by reference); and monoclonal antibodies L27, G28-2, 93-1B3, B-C1 or NU-B2 available from the International Leukocyte Typing Workshop (Valentine et al., In: *Leukocyte Typing III* (McMichael, Ed., p. 440, Oxford University Press (1987)).

Examples of antibodies which bind the CD19 antigen include the anti-CD19 antibodies in Hekman et al. *Cancer Immunol. Immunother.* 32:364-372 (1991) and Vlasveld et al. *Cancer Immunol. Immunother.* 40:37-47 (1995); and the B4 antibody in Kiesel et al. *Leukemia Research II*, 12: 1119 (1987).

The terms "rituximab" or "RITUXAN®" herein refer to the genetically engineered chimeric murine/human monoclonal antibody directed against the CD20 antigen and designated "C2B8" in U.S. Pat. No. 5,736,137, expressly incorporated herein by reference. The antibody is an IgG$_1$ kappa immunoglobulin containing murine light and heavy chain variable region sequences and human constant region sequences. Rituximab has a binding affinity for the CD20 antigen of approximately 8.0 nM.

An "isolated" antagonist is one which has been identified and separated and/or recovered from a component of its natural environment. Contaminant components of its natural environment are materials which would interfere with diagnostic or therapeutic uses for the antagonist, and may include enzymes, hormones, and other proteinaceous or nonproteinaceous solutes. In preferred embodiments, the antagonist will be purified (1) to greater than 95% by weight of antagonist as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antagonist includes the antagonist in situ within recombinant cells since at least one component of the antagonist's natural environment will not be present. Ordinarily, however, isolated antagonist will be prepared by at least one purification step.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

The expression "therapeutically effective amount" refers to an amount of the antagonist which is effective for preventing, ameliorating or treating the autoimmune disease in question.

The term "immunosuppressive agent" as used herein for adjunct therapy refers to substances that act to suppress or mask the immune system of the mammal being treated herein. This would include substances that suppress cytokine production, downregulate or suppress self-antigen expression, or mask the MHC antigens. Examples of such agents include 2-amino-6-aryl-5-substituted pyrimidines (see U.S. Pat. No. 4,665,077, the disclosure of which is incorporated herein by reference); azathioprine; cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or -α antibodies, anti-tumor necrosis factor-α antibodies, anti-tumor necrosis factor-43 antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; TGF-β; streptodornase; RNA or DNA from the host; FK506; RS-61443; deoxyspergualin; rapamycin; T-cell receptor (Cohen et al., U.S. Pat. No. 5,114,721); T-cell receptor fragments (Offner et al., Science, 251: 430-432 (1991); WO 90/11294; Ianeway, Nature, 341: 482 (1989); and WO 91/01133); and T cell receptor antibodies (EP 340,109) such as T10139.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1$\alpha$, IL-2, IL-3, IL-4, IL-5, IL-6, IL-7, IL-8, IL-9, IL-11, IL-12, IL-15; a tumor necrosis factor such as TNF-$\alpha$ or TNF-$\beta$; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery,* Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, $\beta$-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the antagonists disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

II. Production of Antagonists

The methods and articles of manufacture of the present invention use, or incorporate, an antagonist which binds to a B cell surface marker. Accordingly, methods for generating such antagonists will be described here.

The B cell surface marker to be used for production of, or screening for, antagonist(s) may be, e.g., a soluble form of the antigen or a portion thereof, containing the desired epitope. Alternatively, or additionally, cells expressing the B cell surface marker at their cell surface can be used to generate, or screen for, antagonist(s). Other forms of the B cell surface marker useful for generating antagonists will be apparent to those skilled in the art. Preferably, the B cell surface marker is the CD19 or CD20 antigen.

While the preferred antagonist is an antibody, antagonists other than antibodies are contemplated herein. For example, the antagonist may comprise a small molecule antagonist optionally fused to, or conjugated with, a cytotoxic agent (such as those described herein). Libraries of small molecules may be screened against the B cell surface marker of interest herein in order to identify a small molecule which binds to that antigen. The small molecule may further be screened for its antagonistic properties and/or conjugated with a cytotoxic agent.

The antagonist may also be a peptide generated by rational design or by phage display (see, e.g., WO98/35036 published 13 Aug. 1998). In one embodiment, the molecule of choice may be a "CDR mimic" or antibody analogue designed based on the CDRs of an antibody. While such peptides may be antagonistic by themselves, the peptide may optionally be fused to a cytotoxic agent so as to add or enhance antagonistic properties of the peptide.

A description follows as to exemplary techniques for the production of the antibody antagonists used in accordance with the present invention.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with 1/5 to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response. (ii) Monoclonal Antibodies Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium 20=that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, antibodies or antibody fragments can be isolated from antibody phage libraries generated using the techniques described in McCafferty et al., *Nature*, 348: 552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

Human antibodies may also be generated by in vitro activated B cells (see U.S. Pat. Nos. 5,567,610 and 5,229,275).

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science,* 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the B cell. Bispecific antibodies may also be used to localize cytotoxic agents to the B cell. These antibodies possess a B cell marker-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

III. Conjugates and Other Modifications of the Antagonist

The antagonist used in the methods or included in the articles of manufacture herein is optionally conjugated to a cytotoxic agent.

Chemotherapeutic agents useful in the generation of such antagonist-cytotoxic agent conjugates have been described above.

Conjugates of an antagonist and one or more small molecule toxins, such as a calicheamicin, a maytansine (U.S. Pat. No. 5,208,020), a trichothene, and CC1065 are also contemplated herein. In one embodiment of the invention, the antagonist is conjugated to one or more maytansine molecules (e.g. about 1 to about 10 maytansine molecules per antagonist molecule). Maytansine may, for example, be converted to May-SS-Me which may be reduced to May-SH3 and reacted with modified antagonist (Chari et al. *Cancer Research* 52: 127-131 (1992)) to generate a maytansinoid-antagonist conjugate.

Alternatively, the antagonist is conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^1, \alpha_2^1, \alpha_3^1$, N-acetyl-$\gamma_1^1$, PSAG and $\theta_1^1$ (Hinman et al. *Cancer Research* 53: 3336-3342 (1993) and Lode et al. *Cancer Research* 58: 2925-2928 (1998)).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates antagonist conjugated with a compound with nucleolytic activity (e.g. a ribonuclease or a DNA endonuclease such as a deoxyribonuclease; DNase).

A variety of radioactive isotopes are available for the production of radioconjugated antagonists. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antagonist and cytotoxic agent may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antagonist. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the antagonist and cytotoxic agent may be made, e.g. by recombinant techniques or peptide synthesis.

In yet another embodiment, the antagonist may be conjugated to a "receptor" (such streptavidin) for utilization in tumor pretargeting wherein the antagonist-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

The antagonists of the present invention may also be conjugated with a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of such conjugates includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antagonist-abzyme conjugates can be prepared as described herein for delivery of the abzyme to a tumor cell population.

The enzymes of this invention can be covalently bound to the antagonist by techniques well known in the art such as the use of the heterobifunctional crosslinking reagents discussed above. Alternatively, fusion proteins comprising at least the antigen binding region of an antagonist of the invention linked to at least a functionally active portion of an enzyme of the invention can be constructed using recombinant DNA techniques well known in the art (see, e.g., Neuberger et al., *Nature*, 312: 604-608 (1984)).

Other modifications of the antagonist are contemplated herein. For example, the antagonist may be linked to one of a variety of nonproteinaceous polymers, e.g., polyethylene glycol, polypropylene glycol, polyoxyalkylenes, or copolymers of polyethylene glycol and polypropylene glycol.

The antagonists disclosed herein may also be formulated as liposomes. Liposomes containing the antagonist are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

Amino acid sequence modification(s) of protein or peptide antagonists described herein are contemplated. For example, it may be desirable to improve the binding affinity and/or other biological properties of the antagonist. Amino acid sequence variants of the antagonist are prepared by introducing appropriate nucleotide changes into the antagonist nucleic acid, or by peptide synthesis. Such modifications include, for example, deletions from, and/or insertions into and/or substitutions of, residues within the amino acid sequences of the antagonist. Any combination of deletion, insertion, and substitution is made to arrive at the final construct, provided that the final construct possesses the desired characteristics. The amino acid changes also may alter post-translational processes of the antagonist, such as changing the number or position of glycosylation sites.

A useful method for identification of certain residues or regions of the antagonist that are preferred locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antagonist variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antagonist with an N-terminal methionyl residue or the antagonist fused to a cytotoxic polypeptide. Other insertional variants of the antagonist molecule include the fusion to the N- or C-terminus of the antagonist of an enzyme, or a polypeptide which increases the serum half-life of the antagonist.

Another type of variant is an amino acid substitution variant. These variants have at least one amino acid residue in the antagonist molecule replaced by different residue. The sites of greatest interest for substitutional mutagenesis of antibody antagonists include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | giu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antagonist are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antagonist also may be substituted, generally with serine, to improve the oxidative stability of the molecule and prevent aberrant crosslinking. Conversely, cysteine bond(s) may be added to the antagonist to improve its stability (particularly where the antagonist is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7=sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antagonist alters the original glycosylation pattern of the antagonist. By altering is meant deleting one or more carbohydrate moieties found in the antagonist, and/or adding one or more glycosylation sites that are not present in the antagonist.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antagonist is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antagonist (for O-linked glycosylation sites).

Nucleic acid molecules encoding amino acid sequence variants of the antagonist are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antagonist.

It may be desirable to modify the antagonist of the invention with respect to effector function, e.g. so as to enhance antigen-dependent cell-mediated cyotoxicity (ADCC) and/or complement dependent cytotoxicity (CDC) of the antagonist. This may be achieved by introducing one or more amino acid substitutions in an Fc region of an antibody antagonist. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

To increase the serum half life of the antagonist, one may incorporate a salvage receptor binding epitope into the antagonist (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

IV. Pharmaceutical Formulations

Therapeutic formulations of the antagonists used in accordance with the present invention are prepared for storage by mixing an antagonist having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Exemplary anti-CD20 antibody formulations are described in WO98/56418, expressly incorporated herein by reference. This publication describes a liquid multidose formulation comprising 40 mg/mL rituximab, 25 mM acetate, 150 mM trehalose, 0.9% benzyl alcohol, 0.02% polysorbate 20 at pH 5.0 that has a minimum shelf life of two years storage at 2-8° C. Another anti-CD20 formulation of interest comprises 10 mg/mL rituximab in 9.0 mg/mL sodium chloride, 7.35 mg/mL sodium citrate dihydrate, 0.7 mg/mL polysorbate 80, and Sterile Water for Injection, pH 6.5.

Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g. one which binds LFA-1). The effective amount of such other agents depends on the amount of antagonist present in the formulation, the type of disease or disorder or treatment, and other factors discussed above. These are generally used in the same dosages and with administration routes as used hereinbefore or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

V. Treatment with the Antagonist

The composition comprising an antagonist which binds to a B cell surface antigen will be formulated, dosed, and administered in a fashion consistent with good medical practice. Factors for consideration in this context include the particular disease or disorder being treated, the particular mammal being treated, the clinical condition of the individual patient, the cause of the disease or disorder, the site of delivery of the agent, the method of administration, the scheduling of administration, and other factors known to medical practitioners. The therapeutically effective amount of the antagonist to be administered will be governed by such considerations.

As a general proposition, the therapeutically effective amount of the antagonist administered parenterally per dose will be in the range of about 0.1 to 20 mg/kg of patient body weight per day, with the typical initial range of antagonist used being in the range of about 2 to 10 mg/kg.

The preferred antagonist is an antibody, e.g. an antibody such as RITUXAN®, which is not conjugated to a cytotoxic agent. Suitable dosages for an unconjugated antibody are, for example, in the range from about 20 mg/m$^2$ to about 1000 mg/m$^2$. In one embodiment, the dosage of the antibody differs from that presently recommended for RITUXAN®. For example, one may administer to the patient one or more doses of substantially less than 375 mg/m$^2$ of the antibody, e.g. where the dose is in the range from about 20 mg/m$^2$ to about 250 mg/m$^2$, for example from about 50 mg/m$^2$ to about 200 mg/m$^2$.

Moreover, one may administer one or more initial dose(s) of the antibody followed by one or more subsequent dose(s), wherein the mg/m$^2$ dose of the antibody in the subsequent dose(s) exceeds the mg/m$^2$ dose of the antibody in the initial dose(s). For example, the initial dose may be in the range from about 20 mg/m$^2$ to about 250 mg/m$^2$ (e.g. from about 50 mg/m$^2$ to about 200 mg/m$^2$) and the subsequent dose may be in the range from about 250 mg/m$^2$ to about 1000 mg/m$^2$.

As noted above, however, these suggested amounts of antagonist are subject to a great deal of therapeutic discretion. The key factor in selecting an appropriate dose and scheduling is the result obtained, as indicated above. For example, relatively higher doses may be needed initially for the treatment of ongoing and acute diseases. To obtain the most efficacious results, depending on the disease or disorder, the antagonist is administered as close to the first sign, diagnosis, appearance, or occurrence of the disease or disorder as possible or during remissions of the disease or disorder.

The antagonist is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antagonist may suitably be administered by pulse infusion, e.g., with declining doses of the antagonist. Preferably the dosing is given by injections, most preferably intravenous or subcutaneous injections, depending in part on whether the administration is brief or chronic.

One may administer other compounds, such as cytotoxic agents, chemotherapeutic agents, immunosuppressive agents and/or cytokines with the antagonists herein. The combined administration includes coadministration, using separate formulations or a single pharmaceutical formulation, and consecutive administration in either order, wherein preferably there is a time period while both (or all) active agents simultaneously exert their biological activities.

Aside from administration of protein antagonists to the patient the present application contemplates administration of antagonists by gene therapy. Such administration of nucleic acid encoding the antagonist is encompassed by the expression "administering a therapeutically effective amount of an antagonist". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antagonist is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429-4432 (1987); and Wagner et al., *Proc. Natl. Acad. Sci. USA* 87:3410-3414 (1990). For review of the currently known gene marking and gene therapy protocols see Anderson et al., *Science* 256:808-813 (1992). See also WO 93/25673 and the references cited therein.

VI. Articles of Manufacture

In another embodiment of the invention, an article of manufacture containing materials useful for the treatment of the diseases or disorders described above is provided. The article of manufacture comprises a container and a label or package insert on or associated with the container. Suitable containers include, for example, bottles, vials, syringes, etc. The containers may be formed from a variety of materials such as glass or plastic. The container holds or contains a composition which is effective for treating the disease or disorder of choice and may have a sterile access port (for example the container may be an intravenous solution bag or a vial having a stopper pierceable by a hypodermic injection needle). At least one active agent in the composition is the antagonist which binds a B cell surface marker. The label or package insert indicates that the composition is used for treating a patient having or predisposed to an autoimmune disease, such as those listed herein. The article of manufacture may further comprise a second container comprising a pharmaceutically-acceptable diluent buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further details of the invention are illustrated by the following non-limiting Examples. The disclosures of all citations in the specification are expressly incorporated herein by reference.

Example 1

Patients with clinical diagnosis of rheumatoid arthritis (RA) are treated with rituximab (RITUXAN®) antibody. The patient treated will not have a B cell malignancy. Moreover, the patient is optionally further treated with any one or more agents employed for treating RA such as salicylate; nonsteroidal anti-inflammatory drugs such as indomethacin, phenylbutazone, phenylacetic acid derivatives (e.g. ibuprofen and fenoprofen), naphthalene acetic acids (naproxen), pyrrolealkanoic acid (tometin), indoleacetic acids (sulindac), halogenated anthranilic acid (meclofenamate sodium), piroxicam, zomepirac and diflunisal; antimalarials such as chloroquine; gold salts; penicillamine; or immunosuppressive agents such as methotrexate or corticosteroids in dosages known for such drugs or reduced dosages. Preferably however, the patient is only treated with RITUXAN®.

RITUXAN® is administered intravenously (IV) to the RA patient according to any of the following dosing schedules:

(A) 50 mg/m$^2$ IV day 1
150 mg/m$^2$ IV on days 8, 15 & 22
(B) 150 mg/m$^2$ IV day 1
375 mg/m$^2$ IV on days 8, 15 & 22
(C) 375 mg/m$^2$ IV days 1, 8, 15 & 22

The primary response is determined by the Paulus index (Paulus et al. *Athritis Rheum.* 33:477-484 (1990)), i.e. improvement in morning stiffness, number of painful and inflamed joints, erythrocyte sedimentation (ESR), and at least a 2-point improvement on a 5-point scale of disease severity assessed by patient and by physician. Administration of RITUXAN® will alleviate one or more of the symptoms of RA in the patient treated as described above.

Example 2

Patients diagnosed with autoimmune hemolytic anemia (AIHA), e.g., cryoglobinemia or Coombs positive anemia, are treated with RITUXAN® antibody. AIHA is an acquired hemolytic anemia due to auto-antibodies that react with the patient's red blood cells. The patient treated will not have a B cell malignancy.

RITUXAN® is administered intravenously (IV) to the patient according to any of the following dosing schedules:

(A) 50 mg/m$^2$ IV day 1
150 mg/m$^2$ IV on days 8, 15 & 22
(B) 150 mg/m$^2$ IV day 1
375 mg/m$^2$ IV on days 8, 15 & 22
(C) 375 mg/m$^2$ IV days 1, 8, 15 & 22

Further adjunct therapies (such as glucocorticoids, prednisone, azathioprine, cyclophosphamide, vinca-laden platelets or Danazol) may be combined with the RITUXAN® therapy, but preferably the patient is treated with RITUXAN® as a single-agent throughout the course of therapy.

Overall response rate is determined based upon an improvement in blood counts, decreased requirement for transfusions, improved hemoglobin levels and/or a decrease in the evidence of hemolysis as determined by standard chemical parameters. Administration of RITUXAN® will improve any one or more of the symptoms of hemolytic anemia in the patient treated as described above. For example, the patient treated as described above will show an increase in hemoglobin by at least 1 g/dl and an improvement in chemical parameters of hemolysis by 50% or return to normal as measured by serum lactic dehydrogenase, bilirubin.

Example 3

Adult immune thrombocytopenic purpura (ITP) is a relatively rare hematologic disorder that constitutes the most common of the immune-mediated cytopenias. The disease typically presents with severe thrombocytopenia that may be associated with acute hemorrhage in the presence of normal to increased megakaryocytes in the bone marrow. Most patients with ITP have an IgG antibody directed against target antigens on the outer surface of the platelet membrane, resulting in platelet sequestration in the spleen and accelerated reticuloendothelial destruction of platelets (Bussell, J. B. *Hematol. Oncol. Clin. North Am.* (4):179 (1990)). A number of therapeutic interventions have been shown to be effective in the treatment of ITP. Steroids are generally considered first-line therapy, after which most patients are candidates for intravenous immunoglobulin (IVIG), splenectomy, or other medical therapies including vincristine or immunosuppressive/cytotoxic agents. Up to 80% of patients with ITP initially respond to a course of steroids, but far fewer have complete and lasting remissions. Splenectomy has been recommended as standard second-line therapy for steroid failures, and leads to prolonged remission in nearly 60% of cases yet may result in reduced immunity to infection. Splenectomy is a major surgical procedure that may be associated with substantial morbidity (15%) and mortality (2%). IVIG has also been used as second line medical therapy, although only a small proportion of adult patients with ITP achieve remission.

Therapeutic options that would interfere with the production of autoantibodies by activated B cells without the associated morbidities that occur with corticosteroids and/or splenectomy would provide an important treatment approach for a proportion of patients with ITP.

Patients with clinical diagnosis of ITP (e.g. with a platelet count <50,000 μL) are treated with rituximab (RITUXAN®)

antibody, optionally in combination with steroid therapy. The patient treated will not have a B cell malignancy.

RITUXAN® is administered intravenously (IV) to the ITP patient according to any of the following dosing schedules:
(A) 50 mg/m² IV day 1
150 mg/m² IV on days 8, 15 & 22
(B) 150 mg/m² IV day 1
375 mg/m² IV on days 8, 15 & 22
(C) 375 mg/m² IV days 1, 8, 15 & 22

Patients are premedicated with one dose each of diphenhydramine 25-50 mg intravenously and acetaminophen 650 mg orally prior to the infusion of RITUXAN®. Using a sterile syringe and a 21 gauge or larger needle, the necessary amount of RITUXAN® is transferred from the vial into an IV bag containing sterile, pyrogen-free 0.9% Sodium Chloride, USP (saline solution). The final concentration of RITUXAN® is approximately 1 mg/mL. The initial dose infusion rate is initiated at 25 mg/hour for the first half hour then increased at 30 minute intervals by 50 mg/hr increments to a maximum rate of 200 mg/hours. If the first course of RITUXAN® is well tolerated, the infusion rates of subsequent courses start at 50 mg/hour and escalate at 30 minute intervals by 100 mg/hour increments to a maximum rate not to exceed 300 mg/hr. Vital signs (blood pressure, pulse, respiration, temperature) are monitored every 15 minutes×4 or until stable, and then hourly until the infusion is completed.

Overall response rate is determined based upon a platelet count determined on two consecutive occasions two weeks apart following the four weekly treatments of RITUXAN®. Patients treated with RITUXAN® will show improved platelet counts compared to patients treated with placebo. For example, in those patients with platelet count <20,000 µl, an increase in platelet count to 20,000/µl would be considered a response; and for those patients with platelet counts >20,000/µl and clinical evidence of bleeding, a total increase in platelet count by 10,000/µl or more and resolution of symptoms would be considered a response. See, George et al. "Idiopathic Thrombocytopenic Purpura: A Practice Guideline Developed by Explicit Methods for The American Society of Hematology" *Blood* 88:3-40 (1996), expressly incorporated herein by reference.

What is claimed is:

1. A method of treating rheumatoid arthritis in a human comprising: (a) administering to the human more than one intravenous dose of a therapeutically effective amount of rituximab; and (b) administering to the human methotrexate.

2. The method of claim 1, wherein each administration of the rituximab is a dose in the range from about 250 mg/m² to about 1000 mg/m².

3. The method of claim 1, comprising administering to the human a glucocorticosteroid.

4. The method of claim 1, comprising administering an initial dose of the rituximab followed by a subsequent dose, where the mg/m² dose of the rituximab in the subsequent dose exceeds the mg/m² dose of the rituximab in the initial dose.

5. A method of treating rheumatoid arthritis in a human comprising: (a) administering to the human more than one intravenous dose of a therapeutically effective amount of an antibody that binds to the CD20 antigen on human B lymphocytes; and (b) administering to the human methotrexate; wherein the CD20 antibody administration consists of intravenous administration of the CD20 antibody, and the CD20 antibody is rituximab.

6. The method of claim 5, wherein each administration of the antibody is a dose in the range from about 250 mg/m² to about 1000 mg/m².

7. The method of claim 5, comprising administering to the human a glucocorticosteroid.

8. The method of claim 5, comprising administering an initial dose of the antibody followed by a subsequent dose, where the mg/m² dose of the antibody in the subsequent dose exceeds the mg/m² dose of the antibody in the initial dose.

9. A method of treating rheumatoid arthritis in a human comprising: (a) administering to the human more than one intravenous dose of a therapeutically effective amount of an antibody that binds to the CD20 antigen on human B lymphocytes; and (b) administering to the human methotrexate; wherein the therapeutically effective amount of the CD20 antibody is administered intravenously, and the CD20 antibody is rituximab.

10. The method of claim 9, wherein each administration of the antibody is a dose in the range from about 250 mg/m² to about 1000 mg/m².

11. The method of claim 9, comprising administering to the human a glucocorticosteroid.

12. The method of claim 9, comprising administering an initial dose of the antibody followed by a subsequent dose, where the mg/m² dose of the antibody in the subsequent dose exceeds the mg/m² dose of the antibody in the initial dose.

* * * * *